United States Patent
Battaglia

(10) Patent No.: US 10,874,611 B2
(45) Date of Patent: Dec. 29, 2020

(54) CHEMOTACTIC, DRUG-CONTAINING POLYMERSOMES

(71) Applicant: UCL BUSINESS LTD, London (GB)

(72) Inventor: Giuseppe Battaglia, London (GB)

(73) Assignee: UCL BUSINESS LTD, London (GB)

(*) Notice: Subject to any disclaimer, the term of this patent is extended or adjusted under 35 U.S.C. 154(b) by 0 days.

(21) Appl. No.: 16/078,406

(22) PCT Filed: Jan. 27, 2017

(86) PCT No.: PCT/GB2017/050213
§ 371 (c)(1),
(2) Date: Aug. 21, 2018

(87) PCT Pub. No.: WO2017/144849
PCT Pub. Date: Aug. 31, 2017

(65) Prior Publication Data
US 2019/0046445 A1 Feb. 14, 2019

(30) Foreign Application Priority Data
Feb. 25, 2016 (GB) .................................. 1603296.3

(51) Int. Cl.
A61K 9/127 (2006.01)
A61K 38/44 (2006.01)
A61K 47/69 (2017.01)

(52) U.S. Cl.
CPC ............ *A61K 9/1273* (2013.01); *A61K 38/44* (2013.01); *A61K 38/443* (2013.01); *A61K 47/6915* (2017.08); *C12Y 101/03004* (2013.01); *C12Y 111/01006* (2013.01); *Y10S 977/773* (2013.01); *Y10S 977/906* (2013.01)

(58) Field of Classification Search
CPC ..................................................... A61K 9/1273
See application file for complete search history.

(56) References Cited

U.S. PATENT DOCUMENTS

| 6,384,105 B1 | 5/2002 | He et al. |
| 2005/0163743 A1 | 7/2005 | Lewis et al. |
| | (Continued) | |

FOREIGN PATENT DOCUMENTS

| EP | 2 322 227 A1 | 5/2011 |
| JP | H03-31718 B2 | 5/1991 |
| | (Continued) | |

OTHER PUBLICATIONS

A Joseph et al. "Chemotactic synthetic vesicles: Design and applications in blood-brain barrier crossing." Science Advances, vol. 3, 2017, item e1700362, pp. 1-12, published Aug. 2, 2017. (Year: 2017).*

(Continued)

*Primary Examiner* — Issac Shomer
(74) *Attorney, Agent, or Firm* — Kilpatrick Townsend & Stockton LLP

(57) ABSTRACT

The present invention relates to polymersomes that contain an encapsulated drug and that exhibit chemotaxis in response to a chemical stimulus. The chemotactic polymersomes can be targeted in vivo to a location of therapeutic interest with high specificity and selectivity. The present invention also provides related pharmaceutical compositions and therapeutic methods.

9 Claims, 8 Drawing Sheets

Specification includes a Sequence Listing.

(56) References Cited

U.S. PATENT DOCUMENTS

| | | |
|---|---|---|
| 2008/0181939 A1 | 7/2008 | Discher et al. |
| 2008/0311045 A1 | 12/2008 | Hardy |
| 2009/0286247 A1 | 11/2009 | Hirao et al. |
| 2010/0003336 A1 | 1/2010 | Deming et al. |
| 2010/0226955 A1 | 9/2010 | Ludwig et al. |
| 2010/0310660 A1 | 12/2010 | Tsai et al. |
| 2010/0316706 A1 | 12/2010 | Joshi et al. |
| 2011/0065807 A1 | 3/2011 | Radovic-Moreno et al. |
| 2011/0111036 A1 | 5/2011 | Lewis et al. |
| 2011/0150941 A1 | 6/2011 | Battaglia |
| 2011/0172240 A1 | 7/2011 | Milne et al. |
| 2012/0076730 A1 | 3/2012 | Muro Galindo et al. |
| 2015/0079180 A1 | 3/2015 | Karaborni et al. |
| 2015/0110713 A1 | 4/2015 | Manganaro et al. |

FOREIGN PATENT DOCUMENTS

| | | | |
|---|---|---|---|
| WO | 93/01221 A1 | 1/1993 | |
| WO | 94/16749 A1 | 8/1994 | |
| WO | 95/20407 A1 | 8/1995 | |
| WO | 02/028929 A1 | 4/2002 | |
| WO | 03/074090 A2 | 9/2003 | |
| WO | WO-2006080849 A2 * | 8/2006 | ............ C08G 73/00 |
| WO | 2009/061473 A2 | 5/2009 | |
| WO | 2009/138472 A1 | 11/2009 | |
| WO | 2009/138473 A2 | 11/2009 | |
| WO | 2009/138477 A2 | 11/2009 | |
| WO | 2010/148653 A1 | 12/2010 | |
| WO | 2011/005098 A1 | 1/2011 | |
| WO | WO-2011005098 A1 * | 1/2011 | ............... B82Y 5/00 |
| WO | 2011/116132 A1 | 9/2011 | |
| WO | 2012/046994 A2 | 4/2012 | |
| WO | 2013/078562 A2 | 6/2013 | |
| WO | 2014/122646 A1 | 8/2014 | |
| WO | 2015/059180 A2 | 4/2015 | |
| WO | 2016/090111 A1 | 6/2016 | |
| WO | 2017/158382 A1 | 9/2017 | |
| WO | 2017/191444 A1 | 11/2017 | |
| WO | 2017/199023 A1 | 11/2017 | |

OTHER PUBLICATIONS

I Lagzi. "Chemical robotics—chemotactic drug carriers." Central European Journal of Medicine, vol. 8(4), 2013, pp. 377-382. (Year: 2013).*

A Sahari, MA Traore, BE Scharf, B Behkam. "Directed transport of bacteria-based drug delivery vehicles: bacterial chemotaxis dominates particle shape." Biomedical Microdevices, vol. 16 Issue 5, 2014, pp. 717-725. (Year: 2014).*

F Peng, Y Tu, JCM van Hest, DA Wilson. "Self-Guided Supramolecular Cargo-Loaded Nanomotors with Chemotactic Behavior towards Cells." Angewandte Communications International Edition, vol. 54, 2015, pp. 11662-11665. (Year: 2015).*

KT Kim, JJLM Cornelissen, RJM Nolte, JCM van Hest. "A Polymersome Nanoreactor with Controllable Permeability Induced by Stimuli-Responsive Block Copolymers." Advanced Materials, vol. 21, 2009, pp. 2787-2791. (Year: 2009).*

WC Chen, GC Gompleto, DS Sigal, PR Crocker, A Seven, JC Paulson. "In vivo targeting of B-cell lymphoma with glycan ligands of CD22." Blood, vol. 115, No. 23, Jun. 2010, pp. 4778-4786. (Year: 2010).*

Cecchin et al. "Enzyme-driven chemotactic synthetic vesicles", presented at 248th ACS National Meeting: Stimuli-responsive supramolecular, macromolecular and nanostructured systems and biopolymer-driven organization of nanostructures (2014), 1 page. (Year: 2014).*

K. K. Pulicherla and Mahendra Kumar Verma. "Targeting Therapeutics Across the Blood Brain Barrier (BBB), Prerequisite Towards Thrombolytic Therapy for Cerebrovascular Disorders—an Overview and Advancements." AAPS PharmSciTech, vol. 16, No. 2, Apr. 2015, pp. 223-233. (Year: 2015).*

Julia V. Georgieva, Rene P. Brinkhuis, Katica Stojanov, Carel A. G. M. Weijers, Han Zuilhof, Floris P. J. T. Rutjes, Dick Hoekstra, Jan C. M. van Hest, and Inge S. Zuhorn. "Peptide-Mediated Blood-Brain Barrier Transport of Polymersomes." Angewandte Chemie International Edition, 2012, 51, 8339-8342. (Year: 2012).*

Abbas et al. "p21 in Cancer: Intricate Networks and Multiple Activities," (2009) Nat Rev. Cancer 9, 400-414.

Abdelmoshen et al. "Formation of Well-Defined, Functional Nanotubes via Osmotically induced Shape Transformation of Biodegradable Polymersomes," (2016) J. Am. Chem. Soc. 138, 9353-9356.

Anderson "Movement of a semipermeable vesicle through an osmotic gradient," (1983) Phys. Fluids 26, 2871-2879.

Arnold et al. "Enrichment of Single-Walled Carbon Nanotubes by Diameter in Density Gradients," (2005) Nano Letters 5, 713-718.

Arnold et al. "Sorting carbon nanotubes by electronic structure using density differentiation," (2006) Nature Nano 1, 60-65.

Bae et al. "Safety and Efficacy Evaluation of Carnosine, An Endogenous Neuroprotective Agent for Ischemic Stroke," (2013), Stroke, 44, 205-212.

Battaglia and Ryan "Bilayers and Interdigitation in Block Copolymer Vesicles," (2005) J. Am. Chem. Soc. 127(24), 8757-8764.

Battaglia and Ryan "Effect of Amphiphile Size on the Transformation from a Lyotropic Gel to a Vesicular Dispersion,"(2006) Macromolecules 39, 798-805.

Battaglia and Ryan "Neuron-Like Tubular Membranes Made of Diblock Copolymer Amphiphiles," (2006) Angewandte Chemie International Edition 45(13), 2052-2056.

Battaglia and Ryan "Pathways of Polymeric Vesicle Formation," (2006) The Journal of Physical Chemistry B, 110, 102727-10279.

Battaglia and Ryan "The evolution of vesicles from bulk lamellar gels," (2005) Nat. Mater. 4, 869-876.

Battaglia et al. "Polymeric Vesicle Permeability: A Facile Chemical Assay," (2006), Lanmuir 22, 4910.

Battaglia et al. "Wet Nanoscale Imaging and Testing of Polymersomes," (2011) Small 7(14), 2010-2015.

Bieging et al. "Unravelling mechanisms of p53-mediated tumour suppression," (2014) Nat. Rev. Cancer 14, 359-370.

Blanazs et al. "Mechanistic Insights for Block Copolymer Morphologies: How Do Worms Form Vesicles?," (2011) J. Am. Chem. Soc. 133(41), 16581-16587.

Blanazs et al. "Tailoring Macromolecular Expression at Polymersome Surfaces," (2009) Adv. Funct. Mater. 19(18), 2906-2914.

Canton et al. "Fully synthetic polymer vesicles for intracellular delivery of antibodies in live cells," (2013) FASEB J. 27(1), 98-108.

Canton et al. "Scavenger receptors in homeostasis and immunity," (2013) Nature Rev. Imm. 13, 621-634.

Cecchin et al. "Enzyme-driven chemotactic synthetic vesicles", presented at 248th ACS National Meeting: Stimuli-responsive supramolecular, macromolecular and nanostructured systems and biopolymer-driven organization of nanostructures (2014).

Chambon et al. "Facile Synthesis of Methacrylic ABC Triblock Copolymer Vesicles by RAFT Aqueous Dispersion Polymerization," (2012) Macromolecules 45, 5081-5090.

Chambon et al. "How Does Cross-Linking Affect the Stability of Block Copolymer Vesicles in the Presence of Surfactant?," (2012) Langmuir 28, 1196-120.

Chen et al. "High-Purity Separation of Gold Nanoparticle Dimers and Trimers," (2009) Journal of the American Chemical Society 131, 4218-4219.

Christian et al. "Spotted vesicles, striped micelles and Janus assemblies induced by ligand binding" (2009) Nature Mater 8, 843-849.

Colley et al. "Polymersome-Mediated Delivery of Combination Anticancer Therapy to Head and Neck Cancer Cells: 2D and 3D in Vitro Evaluation," (2014) Molecular Pharmaceuticals 11, 1176-1188.

Discher et al. "Polymersomes: Tough Vesicles Made from Diblock Copolymers," (1999) Science 284, 1143-1146.

Du et al. "pH-Sensitive Vesicles Based on a Biocompatible Zwitterionic Diblock Copolymer," (2005) J. Am. Chem. Soc 127(51), 17982-17983.

Ebbens et al. "Size dependence of the propulsion velocity for catalytic Janus-sphere swimmers," (2012) Phys. Rev. E 85 020401(R).

(56) References Cited

OTHER PUBLICATIONS

Gaitzsch et al. "Synthetic Bio-nanoreactor: Mechanical and Chemical Control of Polymersome Membrane Permeability," (2012) Angew. Chem. Int. Ed. 51, 4448-4451.
Gerold et al. "Locking out hepatitis C," (2011) Nature Medicine 17, 542-544.
Ghoreschi et al. "Fumarates improve psoriasis and multiple sclerosis by inducing type II dendritic cells," (2011) J Exp Med 208, 2291-2303.
Giacomelli et al. "Phosphorylcholine-Based pH-Responsive Diblock Copolymer Micelles as Drug Delivery Vehicles: Light Scattering, Electron Microscopy, and Fluorescence Experiments," (2006) Biomacromolecules 7, 817-828.
Gordon "Osmophoresis," (1981) J Phys. Chem. 85, 1753-1755.
Grumelard et al. "Soft nanotubes from amphiphilic ABA triblock macromonomers," (2004) Chemical Communications 13, 1462-1463.
Lee and Feihen "Polymersomes for drug delivery: Design, formation and characterization," (2012) J Control Release 161(2), 473-483.
Linker et al. "Fumaric acid esters exert neuroprotective effects in neuroinflammation via activation of the Nrf2 antioxidant pathway," (2011) Brain 134, 678-692.
Liu et al. "Hydrolysable core crosslinked particles for receptor-mediated pH-sensitive anticancer drug delivery" (2015) New Journal of Chemistry 39(11), 8840-8847.
Loewe et al. "Nuclear Entry of NF-kB/p65 in Human Dimethylfumarate Inhibits TNF-Induced Endothelial Cells," (2002) J. Immunol. 168, 4781-4787.
Lomas et al. "Biomimetic pH Sensitive Polymersomes for Efficient DNA Encapsulation and Delivery," (2007) Adv. Mater. 19, 4238-4242.
Lomas et al. "Efficient Encapsulation of Plasmid DNA in pHSensitive PMPC-PDPA Polymersomes: Study of the Effect of PDPA Block Length on Copolymer—DNA Binding Affinity," (2010) Macromolecular Bioscience 10, 513-530.
Lomas et al. "Non-cytotoxic polymer vesicles for rapid and efficient intracellular delivery," (2008) Faraday discussions 193, 143-159.
Lopresti et al. "Controlling Polymersome Surface Topology at the Nanoscale by Membrane Confined Polymer/Polymer Phase Separation," (2011) ACS NANO 5(3), 1775-1784.
Lopresti et al. "Polymersomes: nature inspired nanometer sized compartments," (2009) J. Mater. Chem. 19, 3576-3590.
Martín et al. "Template Electrosynthesis of High-Performance Graphene Microengines," (2015) Small 11(29), 3568-3574.
Massignani et al "Controlling Cellular Uptake by Surface Chemistry, Size, and Surface Topology at the Nanoscale," (2009) Small 5(21), 2424-2432.
Massignani et al "Enhanced Fluorescence Imaging of Live Cells by Effective Cytosolic Delivery of Probes," (2010) Plos One, 5(5): e10459.
Meng et al. "Stimuli-Responsive Polymersomes for Programmed Drug Delivery," (2009) Biomacromolecules 10(2), 197-209.
Murdoch et al. "Internalization and biodistribution of polymersomes into oral squamous cell carcinoma cells in vitro and in vivo," (2010) Nanomedicine 5, 1025-1036.
Najafi et al. "Biodegradable micelles/polymersomes from fumaric/sebacic acids and poly(ethylene glycol)," (2003) Biomaterials 24(7), 1175-1182.
Napoli et al., "Glucose-oxidase Based Self-Destructing Polymeric Vesicles," (2004) Langmuir 20(9), 3487-3491.
Neculai et al. "Structure of LIMP-2 provides functional insights with implications for SR-BI and CD36," (2013) Nature 504, 172-176.
Paul et al. "Ring-opening copolymerization (ROCOP): synthesis and properties of polyesters and polycarbonates," (2015) Chem. Commun. 51, 6459-6479.
Pearson et al. "Effect of pH and Temperature on PMPC-PDPA Copolymer Self-Assembly," (2013) Macromolecules 46, 1400-1407.
Reiner et al. "Optical manipulation of lipid and polymer nanotubes with optical tweezers," (2004) SPIE 5514, 246-253.
Reiner et al. "Stable and robust polymer nanotubes stretched from polymersomes," (2006) PNAS 103(5), 1173-1177.
Robertson et al. "pH-Sensitive Tubular Polymersomes: Formation and Applications in Cellular Delivery," (2014) ACS Nano 8(5), 4650-4661.
Robertson et al. "Purification of Nanoparticles by Size and Shape," (2016) Scientific Reports 6:27494.
Rosselgong et al. "Thiol-Functionalized Block Copolymer Vesicles," (2012) ACS Macro Letters 1, 1041-1045.
Ruiz-Perez et al. "Molecular engineering of polymersome surface topology,"(2015) Sci Adv 2(4), e1500948).
Saha et al. "Clusters, asters, and collective oscillations in chemotactic colloids," (2014) Phys. Rev. E 89, 062316.
Sanchez-Lopez et al. "Evaluation of liposome populations using a sucrose density gradient centrifugation approach coupled to a continuous flow system," (2009) Analytica Chimica Acta 645, 79-85.
Scannevin et al. "Fumarates Promote Cytoprotection of Central Nervous System Cells against Oxidative Stress via the Nuclear Factor (Erythroid-Derived 2)-Like 2 Pathway," (2012) J, Pharmacol. Exp. Ther. 341, 274-284.
Sharma et al. "Nanocarriers as Promising Drug Vehicles for the Management of Tuberculosis," (2013) Bionanoscience 3(2), 102-111.
Steineweg et al. "Fast and Cost-Effective Purification of Gold Nanoparticles in the 20-250 nm Size Range by Continuous Density Gradient Centrifugation," (2011) Small 7(17), 2443-2448.
Sui et al. "Robust formation of biodegradable polymersomes by direct hydration," (2015) Polymer Chemistry 6(5), 691-696.
Sun et al. "Separation of Nanoparticles in a Density Gradient: FeCo@C and Gold Nanocrystals," (2008) Angewandte Chemie International Edition 48(5), 939-942.
Themistou et al. "Facile synthesis of thiol-functionalized amphiphilic polylactide-methacrylic diblock copolymers," (2014) Polymer Chem 5, 1405-1417.
Tian et al. "LRP-i.-mediated intracellular antibody delivery to the Central Nervous System," (2015) Scientific Reports 5:11990.
Van Oers et al. "Tubular Polymersomes: A Cross-Linker-Induced Shape Transformation," (2013) J. Am. Chem. Soc. 135(44), 16308-16311.
Vlieghe and Khrestchatisky "Peptide-based vectors for blood-brain barrier targeting and delivery of drugs to the central nervous system," (2010) Therapeutic Delivery 1(4), 489-494.
Wang et al. "Encapsulation of Biomacromolecules within Polymersomes by Electroporation," (2012) Angew. Chem., Int. Ed. 51, 11122-11125.
Yakovlev and Deming "Controlled Synthesis of Phosphorylcholine Derivatives of Poly(serine) and Poly(homoserine)," (2015) J. Am. Chem. Soc. 137(12), 4078-4081.
Yealland et al. "Rescue of mitochondrial function in parkin-mutant fibroblasts using drug loaded PMPC-PDPA polymersomes and tubular polymersomes," (2016) Neuroscience Letters 630, 23-29.
Yu et al. "Targeting Strategies for Multifunctional Nanoparticles in Cancer Imaging and Therapy,"(2012) Theranostics 2(1), 3-44.
Cecchin et al. "Enzyme-driven chemotactic synthetic vesicles", slide presentation at the ACS 248th National Meeting, San Francisco, Aug. 2014, 19 pages.

* cited by examiner

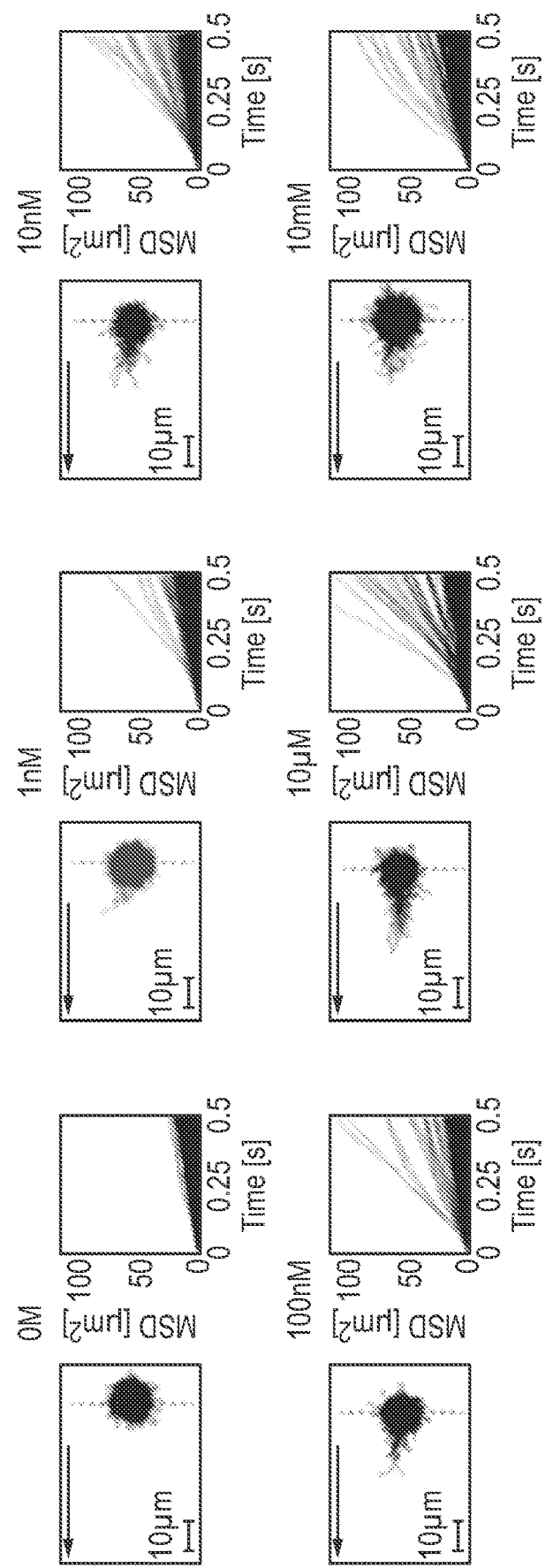

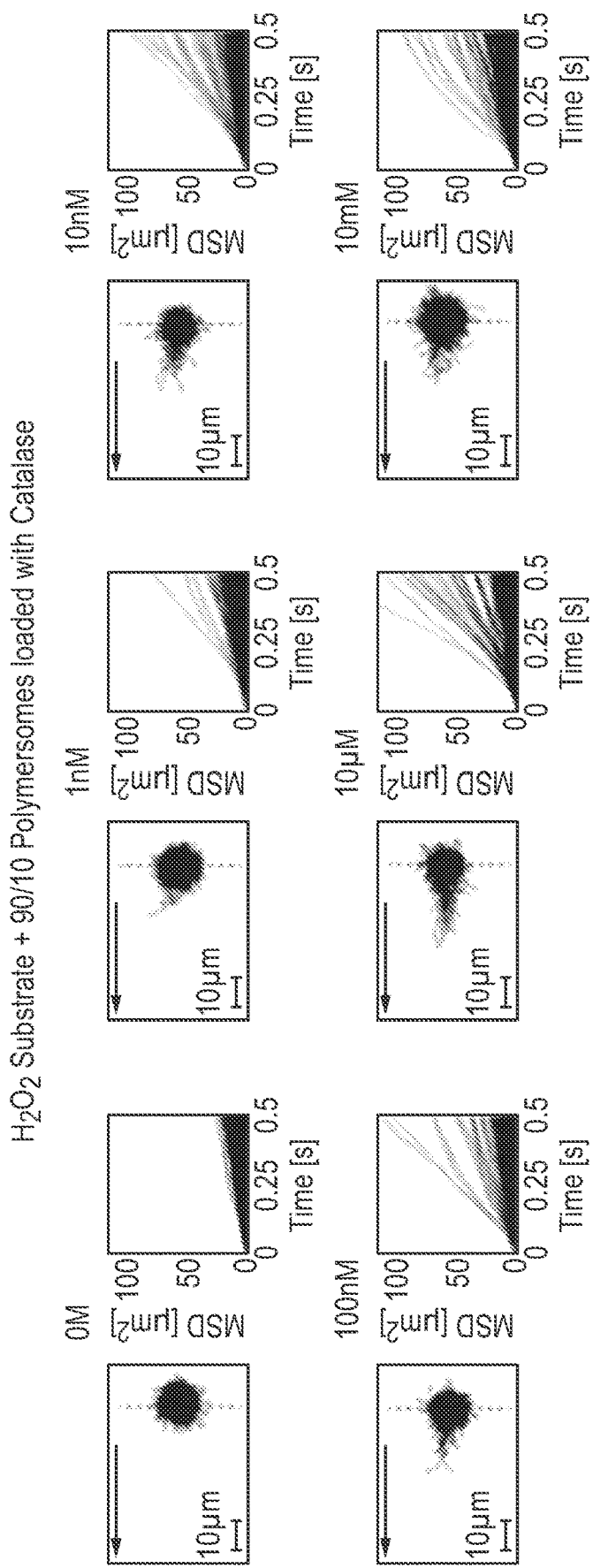
Fig. 3(A Cont.)
H₂O₂ Substrate + 90/10 Polymersomes loaded with Catalase

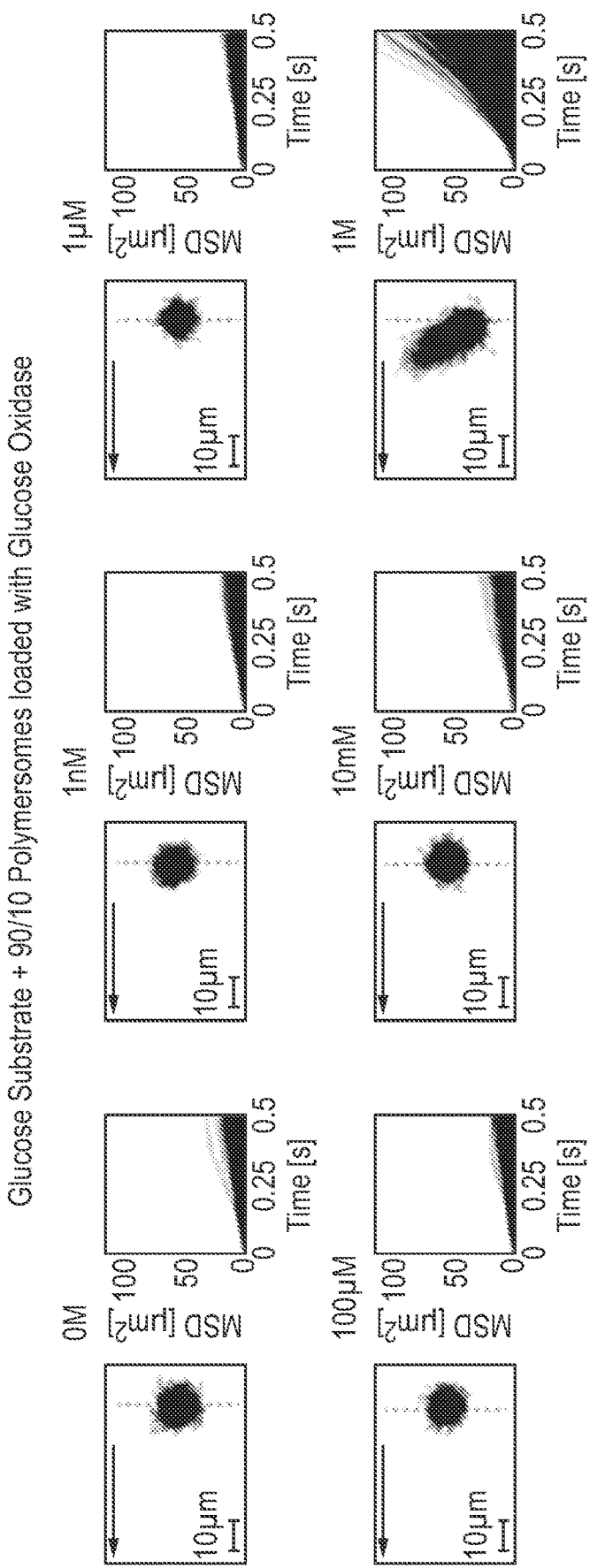

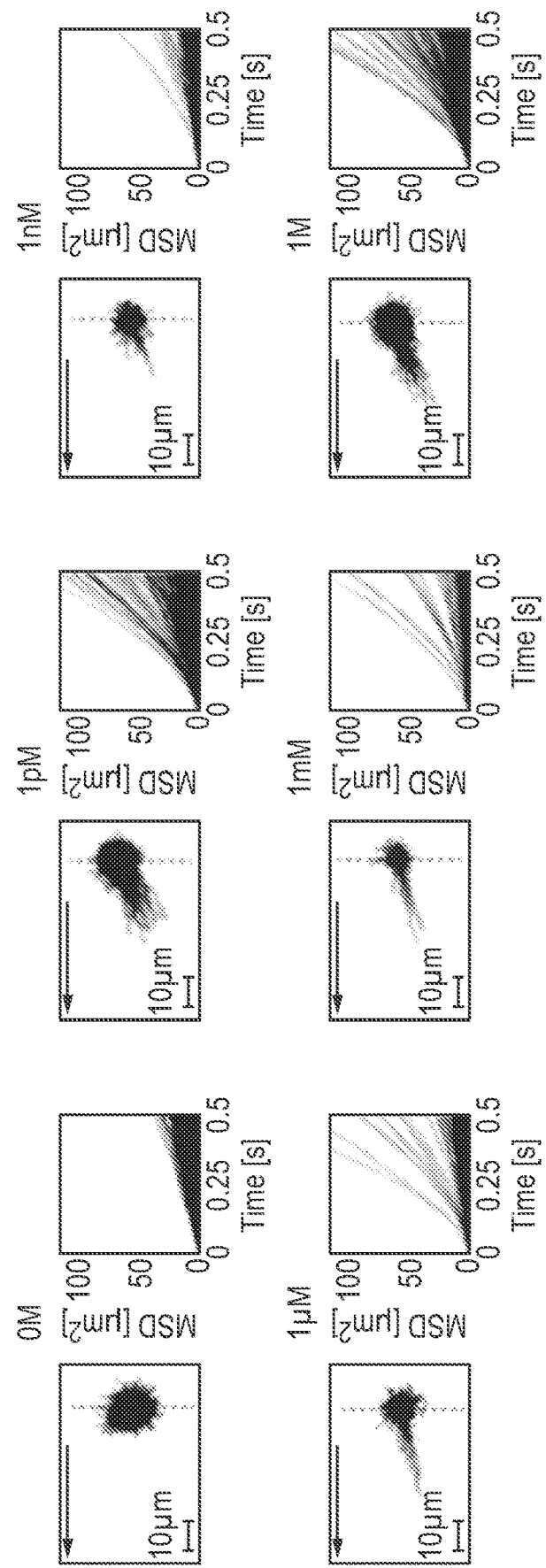

SEQUENCE LISTING

<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Thr Phe Phe Tyr Gly Gly Ser Arg Gly Lys Arg Asn Asn Phe Lys Thr
1               5                   10                  15

Glu Glu Tyr

CHEMOTACTIC, DRUG-CONTAINING POLYMERSOMES

CROSS-REFERENCE TO RELATED APPLICATIONS

This application is a national stage application under 35 U.S.C. § 371 of International Patent Application No. PCT/GB2017/050213, filed Jan. 27, 2017, which claims priority to GB Application No. 1603296.3, filed Feb. 25, 2016, the disclosures both of which are hereby incorporated by reference for all purposes in their entireties.

SEQUENCE LISTING

The instant application contains a Sequence Listing which has been submitted electronically in ASCII format and is hereby incorporated by reference in its entirety. Said ASCII copy, created on Jul. 31, 2020, is named 092340-006300US-1101202_SL.txt and is 644 bytes in size.

FIELD OF THE INVENTION

The present invention relates to chemotactic, drug-containing polymersomes, as well as pharmaceutical compositions containing such polymersomes.

BACKGROUND OF THE INVENTION

Drug formulation plays a critical role in the development of commercial medicines. Primary goals for a formulation chemist include maximising the therapeutic efficacy conferred by the drug being formulated and ensuring patient safety, for example by minimising drug dosage and/or delivery of drug to non-target tissues. A vast range of formulation techniques has been developed for administering medicinal compounds to patients.

Over recent decades, nanocarriers have been the subject of significant interest. It has been suggested that formulations based on compositions of matter such as liposomes, micelles and polymeric nanoparticles may provide for improvements in the therapeutic index of existing drugs, as well as enabling new therapies. Such applications are based on a number of underlying assumptions, including that the nanocarriers: (i) are capable of encapsulating and subsequently releasing the desired active molecules; (ii) are biocompatible, non-immunogenic, and bioresorbable into components that are metabolised once the nanocarrier's function has been fulfilled; (iii) have the appropriate physicochemical properties to ensure cell selectivity; and (iv) are able to penetrate tissues and organs of interest.

Selectivity is major concern in the development of drug delivery systems in general. Systemic administration of drug molecules, in particular, is often associated with significant deleterious, and in some cases prohibitive, side effects. Even when formulations are adapted to provide for targeting of the drug to tissues of interest, side effects can persist. For example, the use of targeting moieties such as peptides, aptamers, vitamins, glycols, and the whole or fragments of antibodies can achieve exceptionally high target specificity, but the targeting occurs only at a very local level, with the effectiveness of the drug still being fundamentally limited by diffusion-controlled processes. Tissue penetration is also an issue for most therapeutics and is a particularly serious issue for nanoparticles on account of their high mass.

New formulation techniques for the targeted delivery of drugs are therefore needed. Particularly desirable would be formulations having high selectivity for tissues of interest and/or with a high capacity to penetrate tissues of interest.

SUMMARY OF THE INVENTION

It has now been found that drugs can be delivered to target tissues in a highly selective and effective manner by encapsulating them in a specific type of polymersome. In particular, the polymersome is engineered so that it is capable of demonstrating chemotaxis (movement in response to an external chemical stimulus) in vivo.

Unlike known target-specific substances such as ADCs (antibody-drug conjugates) or even "regular" polymersomes whose surfaces are functionalised with targeting moieties, the ability of the chemotactic, drug-containing polymersome of the invention to reach the desired tissues is not limited by conventional diffusion processes. Instead the chemotactic, drug-containing polymersome of the invention exhibits a combination of osmophoresis and self-diffusiophoresis that has been found to lead to significant advantages in an in vivo environment in a clinical setting.

In particular, it has been found that the in vivo chemotactic motion of the drug-containing polymersome drives the polymersome, and hence the drug cargo, away from the normal flow path along capillaries and towards the blood vessel wall interface of the capillaries. When this is combined with targeting capability, the amount of polymersomes biding to their target increases by several folds.

Substantial enhancements in the efficiency with which drug can be delivered to target tissues from the systemic blood circulatory system have consequently been observed. This renders the formulations of the invention surprisingly beneficial for achieving the efficient and highly selective delivery of a drug to a target tissue.

Specifically, the present invention therefore provides a chemotactic, drug-containing polymersome that comprises: (a) a polymersome; (b) an enzyme encapsulated within the polymersome; and (c) a drug encapsulated within the polymersome; wherein: (i) the polymersome is permeable to a signalling molecule that is a substrate for the enzyme; (ii) the enzyme is capable of converting the signalling molecule into one or more product molecules; (iii) the polymersome is permeable to the one or more product molecules; and (iv) the permeability to the one or more product molecules of a first region of the polymersome is greater than the permeability to the one or more product molecules of a second region of the polymersome, the second region being diametrically opposed to the first region.

The present invention further provides a pharmaceutical composition comprising: a plurality of the chemotactic, drug-containing polymersomes of the present invention; and one or more pharmaceutically acceptable excipients or diluents.

The present invention additionally provides a chemotactic, drug-containing polymersome of the present invention, for use as a medicament.

BRIEF DESCRIPTION OF THE FIGURES

FIG. 3 shows single particle analysis of chemotactic polymersomes. (A) Three different combinations of 90/10 PMPC/PEO polymersomes loaded with catalase and exposed to hydrogen peroxide gradients. (B) Polymersomes loaded with glucose oxidase. (C) Polymersomes loaded with glucose oxidases and catalase both exposed to different glucose gradients. The paths of the polymersomes were analysed using Nanoparticle Tracking Analysis (NTA). Data is plotted as traces from 0 s to 0.5 s from a normalised origin and their corresponding Mean Square Displacement (MSD) as a function of time for various substrate gradients. (In the trace plots the arrow shows the chemical gradient direction).

DETAILED DESCRIPTION OF THE INVENTION

Polymersome

Figure 1:
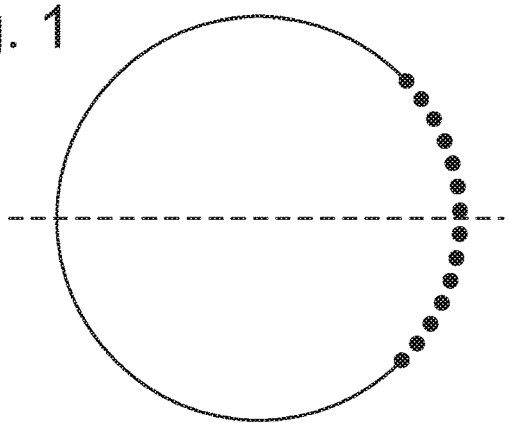
FIG. 1 shows a schematic representation of a polymersome comprising a first region (bold dotted line) of high permeability and a diametrically opposed second region (solid line) of low permeability, with the dashed line indicating a straight line passing through a point on the first region, the geometric centre of the polymersome and a point on the second region.

Polymersomes are synthetic vesicles formed from amphiphilic block copolymers. Examples of polymersomes are described in US 2010/0003336 A1, the contents of which are herein incorporated by reference in their entirety. Over the last fifteen years they have attracted significant research attention as versatile carriers because of their colloidal stability, tuneable membrane properties and ability in encapsulating or integrating other molecules (for one representative review article, see *J Control Release* 2012 161(2) 473-83, the contents of which are herein incorporated by reference in their entirety).

The polymersome used in the present invention is typically a self-assembled structure. Polymersomes typically comprise an amphiphilic block copolymer, i.e. a block copolymer that comprises a hydrophilic block and a hydrophobic block. As explained in more detail elsewhere herein, in the polymersomes of the present invention the polymersome comprises at least two such amphiphilic block copolymers, which are different from one another.

Such copolymers are able to mimic biological phospholipids. Molecular weights of these polymers are much higher than naturally-occurring phospholipid-based surfactants such that they can assemble into more entangled membranes (*J. Am. Chem. Soc.* 2005, 127, 8757, the contents of which are herein incorporated by reference in their entirety), providing a final structure with improved mechanical properties and colloidal stability. Furthermore, the flexible nature of the copolymer synthesis allows the application of different compositions and functionalities over a wide range of molecular weights and consequently of membrane thicknesses. Thus the use of these block copolymers as delivery vehicles offers significant advantages.

Polymersomes are often substantially spherical. Polymersomes typically comprise a bilayered membrane. The bilayer is generally formed from two layers of amphiphilic molecules, which align to form an enclosed core with hydrophilic head groups facing the core and the exterior of the vesicle, and hydrophilic tail groups forming the interior of the membrane.

A typical (largest) diameter of a polymersome is in the range 50 to 5000 nm. More typically, the diameter is in the range 50 to 1000 nm. Polymersomes having a diameter in this range are normally termed "nanopolymersomes" or "nanovesicles". The nanopolymersomes are preferably substantially spherical in shape. Typically, the nanopolymersomes have a number average diameter of less than 300 nm, preferably less than 250 nm, most preferably less than 200 nm or 150 nm.

The thickness of the bilayer is generally between 2 and 50 nm, more typically between 2 and 20 nm (for instance between 5 and 20 nm). These dimensions can routinely be measured, for example by using Transmission Electron Microscopy (TEM) and/or and Small Angle X-ray Scattering (SAXS) (see, for example, *J. Am. Chem. Soc.* 2005, 127, 8757, the contents of which are herein incorporated by reference in their entirety).

As explained in more detail herein, different regions of the polymersome, which are formed from different copolymers, typically have different bilayer thicknesses. Preferably the thickness of the polymersome bilayer of the first region is from 1 to 10 nm, more preferably from 2 to 5 nm. Preferably the thickness of the polymersome bilayer of the second region is from 5 to 50 nm, for instance from 10 to 40 nm. More preferably the thickness of the polymersome bilayer of the second region is from 5 to 20 nm. Preferably the thickness of the polymersome bilayer of the first region is less than the thickness of the polymersome bilayer of the second region. Alternatively, the copolymers can have same thickness but different chemical compositions, which in turn create two different permeabilities with one copolymer forming a bilayer which is less permeable than the other.

In aqueous solution, normally an equilibrium exists between different types of structures, for instance between polymersomes and micelles. It is preferred that at least 80%, more preferably at least 90% or 95% by weight and most preferably all of the structures in solution are present as polymersomes. This can be achieved using the methods outlined herein.

The polymersome of the present invention has a first region and a second region. The first region and the second region are diametrically opposed to one another. The first region is a first region on the external surface of the polymersome. The second region is a second region on the external surface of the polymersome. By "the second region being diametrically opposed to the first region" is meant that a straight line can (notionally) be drawn from a point on the second region that passes through both the geometric centre of the polymersome and a point on the first region. Such a straight line is shown schematically in FIG. 1.

For the avoidance of doubt, provided that such a line can be drawn, it is not relevant whether one or more other straight lines could notionally be drawn from a point on the second region that pass through the geometric centre of the polymersome but that do not pass through a point on the first region. For example, a line could be drawn on top to bottom on FIG. 1 that does not pass through any point on the first region. Nonetheless, the first and second regions in FIG. 1 are diametrically opposed.

The first region of the polymersome typically comprises a first polymer, which is usually a first amphiphilic block copolymer that comprises a first hydrophilic block and a first hydrophobic block. The second region of the polymersome typically comprises a second polymer, which is usually a second amphiphilic block copolymer that comprises a second hydrophilic block and a second hydrophobic block.

The second polymer is different from the first polymer. Typically the monomeric content of the second polymer is different from the monomeric content of the first polymer. The differing monomeric content may be a difference in the relative proportion of hydrophilic and hydrophobic blocks, wherein the monomers themselves are the same in the first and second polymers. More usually, though, the first polymer contains one or more monomers that are not present in the second polymer.

Typically both the first polymer and the second polymer are capable of forming polymersomes in the absence of the other polymer. Alternatively, it is possible for the polymersome to comprise a first polymer and a second polymer where the first polymer forms the polymersome and the second polymer provides differential and asymmetric permeability, for example if a first polymer is combined with a second polymer which forms a membrane nanopore.

It is known that when two different polymersome-forming copolymers are mixed to form a hybrid vesicle they phase-separate and thus give rise to polymersomes that contain discrete regions corresponding to the discrete copolymers. For example, this phenomenon is described in detail in *ACS NANO*, 5(3), 1775-1784 2011, the content of which is herein incorporated by reference in its entirety. The polymersomes of the present invention can be readily manufactured by applying these known synthetic principles.

The permeability to the one or more product molecules of the first region of the polymersome is greater than the permeability to the one or more product molecules of the second region of the polymersome. This difference in permeability is typically achieved by making use of a first polymer that is capable of forming a polymersome and a second polymer that is capable of forming a polymersome, wherein a polymersome consisting of the first polymer is more permeable to the product molecules than a polymersome consisting of the second polymer. As will be readily appreciated, the required difference in permeability is thus achieved by selecting suitable first and second polymers. Non-limiting examples of polymers that form polymersomes that either have high or low permeability are described in more detail in the following disclosure.

The polymersome is thus permeable to the one or more product molecules, which means that they are able to depart from the polymersome after being produced by the reaction between the signalling molecule and the enzyme. Furthermore, in view of the difference in permeability between the first and second regions of the polymersome, the one or more product molecules depart preferentially through the first region of the polymersome. The asymmetric expulsion of the product molecules results in chemotaxis of the polymersome.

The polymersome is also permeable to the signalling molecule. Typically the signalling molecule is capable of entering the polymersome at least through the first region, although the polymersome may also have first and second regions that are both permeable (either to differing or the same extent) to the signalling molecule.

It is preferable to control the ratio of the first and second polymers so that the minor polymer component segregates to form substantially a single domain. Typically the first polymer is present as the minor polymer component. Such a single domain is typically isolated on one side of the polymersome, giving rise to an asymmetric polymersome having a "patch" region of first polymer, as illustrated schematically in FIG. 1.

Preferably the molar ratio of the first polymer to the second polymer in the polymersome is less than 1:1 (i.e. for each mole of second polymer there is less than one mole of first polymer). More preferably the molar ratio of the first polymer to the second polymer in the polymersome is less than 1:2 (i.e. for each two moles of second polymer there is less than one mole of first polymer). More preferably still the molar ratio of the first polymer to the second polymer in the polymersome is less than 1:4 (i.e. for each four moles of second polymer there is less than one mole of first polymer). For example, this molar ratio may be lower than 1:5 or even lower than 1:8.

Preferably, though, this molar ratio is at least 1:40, more preferably at least 1:30 and more preferably still at least 1:20 (i.e. for each forty, thirty or twenty moles of second polymer, respectively, there is at least one mole of first polymer).

For example, the molar ratio of the first polymer to the second polymer in the polymersome may be at least 1:40 but less than 1:1, more preferably at least 1:30 but less than 1:2 and more preferably still at least 1:20 but less than 1:4. For instance, the molar ratio may be from 1:10 to 1:8, such as about 1:9.

The polymersome is preferably capable of dissociating and releasing the encapsulated drug once it has reached the tissue of interest (i.e., the target tissue). Non-limiting, exemplary tissues of interest are discussed in more detail later and include cells (e.g. CNS cells) beyond the blood-brain barrier, immune cells and cancer cells. Preferably the polymersome is capable of dissociating and releasing the encapsulated drug after it has been internalised, via endocytosis, within a target cell (e.g. a CNS cell, an immune cell or a cancer cell).

Dissociation may be promoted by a variety of mechanisms, such as pH sensitivity of the block copolymer, thermal sensitivity of the block copolymer and hydrolysis (i.e. water sensitivity of the block copolymer). Typically, the promotion is by pH sensitivity of the block copolymer. It is thus preferred that at least one of the first region and second region (preferably at least the second region) of the polymersome comprises an amphiphilic copolymer whose hydrophilic or hydrophobic block, preferably the hydrophobic block, has a pendant group with a pKa in the range 3.0 to 6.9. The process of endocytosis includes a reduction in the local pH experienced by the polymersome from around pH 7.4 to around pH 5-6. This pH drop is sufficient to trigger disintegration of the polymersome and release of internalised content. Examples of such pendant groups include zwitterionic groups X as defined herein.

By pKa, is meant the pH where half of the pendant groups are ionised. pKa can be determined by a variety of methods including pH titration followed by potentiometric titration, UV spectroscopy and Dynamic Light Scattering (DLS). An appropriate method should be selected to measure the pKa according to the copolymer which is being analysed and its solubility in the test media.

DLS is a particularly preferred method for measuring pKa. As indicated in *J. Am. Chem. Soc* 2005 127 17982-17983, the contents of which are herein incorporated by reference in their entirety, the DLS signal from a copolymer, such as $PMPC_{25}$-b-$PDPA_{20}$ copolymer, in water varies with pH. At a certain pH the signal rapidly increases as the copolymer undergoes a transition from being molecularly deassociated to associated. The pKa is taken as the pH of the mid-point of this rapid increase. These experiments are described further in *Biomacromolecules* 2006, 7, 817-828, the contents of which are herein incorporated by reference in their entirety. In this reference, the experiments are performed on micelles of PMPC-b-PDPA block copolymer, but the techniques may also be applied when the phase transition involves polymersome formation.

The pKa of a group in a polymer is determined on the basis of a polymer system (and not assumed to be the same as the pKas of similar moieties in non-polymeric systems).

The hydrophobic block of a copolymer comprised in the polymersome (e.g. corresponding to the second region/the second polymer) may also comprise pendant cationisable moieties as pendant groups. Cationisable moieties are, for instance, primary, secondary or tertiary amines, capable of being protonated at pHs below a value in the range 3 to 6.9. Alternatively the group may be a phosphine.

Preferably, the pKa of the pendant groups is in the range 4.0 to 6.9, more preferably 5.5 to 6.9. The polymersomes are correspondingly capable of disassociating in such pH ranges.

Some illustrative polymers suitable for use in constructing the polymersomes of the present invention are now described. It is important at the outset to emphasise that these polymers represent non-limiting examples of polymers that can be used. Polymersomes having the essential features set out in the claims of this application can be constructed by making use of these polymers or other polymers, for example other polymers that are known to be suitable for forming polymersomes.

First, a discussion is provided of some illustrative polymers for constructing the second polymer, i.e. the polymer comprised in the second region of the polymersome of the invention, which has lower permeability than the first region.

The hydrophobic block of the second polymer may preferably have a degree of polymerisation of at least 50, more preferably at least 70. Preferably, the degree of polymerisation of this hydrophobic block is no more than 250, even more preferably, no more than 200. Typically, the degree of polymerisation of the hydrophilic block of the second polymer is at least 15, more preferably at least 20. It is preferred that the ratio of the degree of polymerisation of the hydrophilic to hydrophobic block is in the range 1:2.5 to 1:8. All of these limitations promote polymersome, rather than micelle formation.

The hydrophilic block may be based on condensation polymers, such as polyesters, polyamides, polyanhydrides, polyurethanes, polyethers (including polyalkylene glycols, especially PEG), polyimines, polypeptides, polyureas, polyacetals and polysaccharides, but preferably the hydrophilic block is based on a radical polymerised addition polymer of ethylenically unsaturated monomers. The hydrophilic block may have zwitterionic pendant groups, in which case the zwitterionic pendant groups may be present in the monomers and remain unchanged in the polymerisation process. It is alternatively possible to derivatise a functional pendant group of a monomer to render it zwitterionic after polymerisation.

In one illustrative embodiment, the hydrophilic block of the second polymer is formed from ethylenically-unsaturated zwitterionic monomers. Non-limiting suitable ethylenically unsaturated zwitterionic monomers have the general formula (I)

$$YBX \quad (I),$$

in which:

Y is an ethylenically unsaturated group selected from  $H_2C=CR—CO-A-$, $H_2C=CR—C_6H_4-A^1-$, $H_2C=CR—CH_2-A^2-$, $R^2O—CO—CR=CR—CO—O—$, $RCH=CH—CO—O—$, $RCH=C(COOR^2)CH_2—CO—O—$,

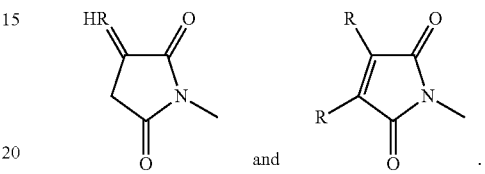

and

A is —O— or $NR^1$;
$A^1$ is selected from a bond, $(CH_2)_LA^2$ and $(CH_2)_LSO_3^-$ in which L is 1 to 12;
$A^2$ is selected from a bond, —O—, —O—CO—, —CO—O—, —CO—$NR^1$—, —$NR^1$—CO—, —O—CO—$NR^1$— and —$NR^1$—CO—O—;
R is hydrogen or $C_{1-4}$ alkyl;
$R^1$ is hydrogen, $C_{1-4}$ alkyl or BX;
$R^2$ is hydrogen or $C_{1-4}$ alkyl;
B is a bond, or a straight or branched alkanediyl, alkylene oxaalkylene, or alkylene (oligooxalkylene) group, optionally containing one or more fluorine substituents; and
X is a zwitterionic group.

Preferably X is an ammonium, phosphonium, or sulphonium phosphate or phosphonate ester zwitterionic group, more preferably a group of the general formula (II)

in which the moieties $A^3$ and $A^4$, which are the same or different, are —O—, —S—, —NH— or a valence bond, preferably —O—, and $W^+$ is a group comprising an ammonium, phosphonium or sulphonium cationic group and a group linking the anionic and cationic moieties which is preferably a $C_{1-12}$-alkanediyl group.

Preferably $W^+$ is a group of formula —$W^1$—$N^+R^3_3$, —$W^1$—$P^+R^4_3$, —$W^1$—$S^+R^4_2$ or —$W^1$—$Het^+$ in which:

$W^1$ is alkanediyl of 1 or more, preferably 2-6 carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups;

the groups $R^3$ are the same or different and each is hydrogen or alkyl of 1 to 4 carbon atoms, preferably methyl, or aryl, such as phenyl, or two of the groups $R^3$ together with the nitrogen atom to which they are attached form an aliphatic heterocyclic ring containing from 5 to 7 atoms, or two or more of the groups R³ together with the nitrogen atom to which they are attached form a heteroaromatic ring having 5 to 7 atoms, either of which rings may be fused with another saturated or unsaturated ring to form a fused ring structure containing from 5 to 7 atoms in each ring, and optionally one or more of the groups R³ is substituted by a hydrophilic functional group;

the groups R⁴ are the same or different and each is R³ or a group OR³,

Het is an aromatic nitrogen-, phosphorus- or sulphur-, preferably nitrogen-, containing ring, for example pyridine.

Monomers in which X is of the general formula in which W⁺ is W¹N+R³₃ may be made as described in WO-A-9301221, the contents of which are herein incorporated by reference in their entirety. Phosphonium and sulphonium analogues are described in WO-A-9520407 and WO-A-9416749, the contents of both of which are herein incorporated by reference in their entirety.

The group of the formula (II) has a preferred general formula (III)

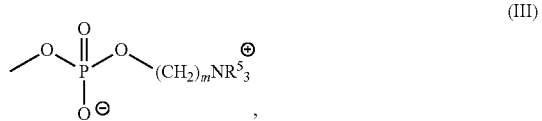

(III)

where the groups R⁵ are the same or different and each is hydrogen or $C_{1-4}$ alkyl, and m is from 1 to 4. The groups R⁵ are preferably the same, for example they are preferably all methyl.

In phosphobetaine based groups, X may have the general formula (IV)

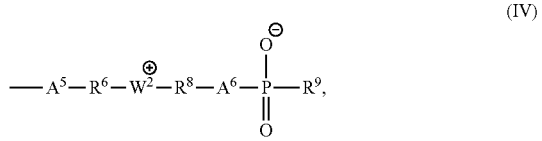

(IV)

in which:

A⁵ is a bond, —O—, —S— or —NH— (preferably —O—);

R⁶ is a bond or alkanediyl, —C(O)-alkanediyl- or —C(O)NH-alkanediyl- (wherein R⁶ is preferably alkanediyl; and wherein alkanediyl is preferably $C_{1-6}$ alkanediyl);

W² is SR⁷, PR⁷₂ or NR⁷₂, wherein the or each group R⁷ is hydrogen or alkyl of 1 to 4 carbon atoms or the two groups R⁷ together with the heteroatom to which they are attached form a heterocyclic ring of 5 to 7 atoms;

R⁸ is alkanediyl of 1 to 20, preferably 1 to 10, more preferably 1 to 6 carbon atoms;

A⁶ is a bond, NH, S or O, preferably O; and

R⁹ is a hydroxyl, $C_{1-12}$ alkyl, $C_{1-12}$ alkoxy, $C_{7-18}$ aralkyl, $C_{7-18}$ aralkoxy, $C_{6-18}$ aryl or $C_{6-18}$ aryloxy group.

Monomers comprising a group of the general formula (IV) may be made by methods as described in JP-B-03-031718, the content of which is herein incorporated by reference in its entirety, in which an amino substituted monomer is reacted with a phospholane.

In compounds comprising a group of the general formula (IV), it is preferred that: A⁵ is a bond; R⁶ is a $C_{2-6}$ alkanediyl; W² is NR⁷₂; each R⁷ is $C_{1-4}$ alkyl; R⁸ is $C_{2-6}$ alkanediyl; A⁶ is O; and R⁹ is $C_{1-4}$ alkoxy.

Alternatively X may be a zwitterion in which the anion comprises a sulphate, sulphonate or carboxylate group.

One example of such a group is a sulphobetaine group, of the general formula (V)

(V)

where the groups R¹⁰ are the same or different and each is hydrogen or $C_{1-4}$ alkyl and s is from 2 to 4. Preferably the groups R¹⁰ are the same. It is also preferable that at least one of the groups R¹⁰ is methyl, and more preferable that the groups R¹⁰ are both methyl. Preferably s is 2 or 3, more preferably 3.

Another example of a zwitterionic group having a carboxylate group is an amino acid moiety in which the alpha carbon atom (to which an amine group and the carboxylic acid group are attached) is joined through a linker group to the backbone of the biocompatible polymer.

Such groups may, for example, be represented by the general formula (VI)

(VI)

in which A⁷ is a bond, —O—, —S— or —NH— (preferably —O—); R¹¹ is a bond or alkanediyl, —C(O)alkanediyl- or —C(O)NHalkanediyl- (wherein alkanediyl is preferably $C_{1-6}$ alkanediyl; wherein R¹¹ is preferably alkanediyl); and the groups R¹² are the same or different and each is hydrogen or alkyl of 1 to 4 carbon atoms, preferably methyl, or two or three of the groups R¹², together with the nitrogen to which they are attached, form a heterocyclic ring of from 5 to 7 atoms, or the three group R¹² together with the nitrogen atom to which they are attached form a fused ring heterocyclic structure containing from 5 to 7 atoms in each ring.

Another example of a zwitterion having a carboxylate group is a carboxy betaine —N+(R¹³)₂(CH₂)ᵣCOO⁻ in which the R¹³ groups are the same or different and each is hydrogen or $R_{1-4}$ alkyl and r is 2 to 6, preferably 2 or 3.

In the zwitterionic monomer of the general formula (I) it is preferred that the ethylenic unsaturated group Y is H₂C=CR—CO-A-. Such acrylic moieties are preferably methacrylic, that is in which R is methyl, or acrylic, in which R is hydrogen. Whilst the compounds may be (meth)acrylamido compounds (in which A is NR¹), in which case R¹ is preferably hydrogen, or less preferably, methyl, most preferably the compounds are esters, that is in which A is O.

In monomers of the general formula (I), especially where Y is the preferred (alk)acrylic group, B is most preferably an alkanediyl group. Whilst some of the hydrogen atoms of such group may be substituted by fluorine atoms, preferably B is an unsubstituted alkanediyl group, most preferably a straight chain group having 2 to 6 carbon atoms.

A particularly preferred zwitterionic monomer is 2-methacryloyloxyethyl-phosphorylcholine (MPC). Mixtures of zwitterionic monomers each having the above general formula may be used, as can mixtures of other hydrophilic monomers described herein.

The hydrophobic block of the second polymer may be formed of condensation polymers, such as polyethers (including polyalkylene glycols), polyesters, polyamides, polyanhydrides, polyurethanes, poiyimines, polypeptides, polyureas, polyacetals, or polysiloxanes. One example of a suitable hydrophobic block is polyalkylene oxide, usually polypropylene oxide, that is the same type of block as has been used in the well-studied Pluronic/Poloxamer based systems. One type of highly hydrophobic block is poly(dimethylsiloxane). In one preferred embodiment the type of polymer forming the hydrophobic block is the same as that forming the hydrophilic block. Preferably the polymer is formed by radical polymerisation of ethylenically unsaturated monomers.

Illustrative, suitable monomers from which the hydrophobic block may be formed have the general formula (VII)

$$Y^1B^1Q \quad \text{(VII)},$$

in which $Y^1$ is selected from $H_2C=CR^{14}$—CO-$A^8$-, $H_2C=CR^{14}$—$C_6H_4$-$A^9$-, $H_2C=CR^{14}$—$CH_2A^{10}$-, $R^{16}O$—CO—$CR^{14}$=$CR^{14}$—CO—O—, $R^{14}CH$=CH—CO—O—, $R^{14}CH$=C(COOR$^{16}$)CH$_2$—CO—O—,

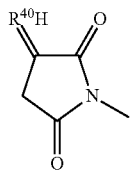 and 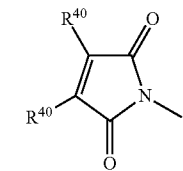 ;

$A^8$ is —O— or —NR$^{15}$—;
$A^9$ is selected from a bond, $(CH_2)_qA_{10}$ and $(CH_2)_qSO_3^-$ in which q is 1 to 12;
$A^{10}$ is selected from a bond, —O—, —O—CO—, —CO—O—, —CO—NR$^{15}$—, —NR$^{15}$—CO—, —O—CO—NR$^{15}$—, —NR$^{15}$—CO—O—;
$R^{14}$ is hydrogen or $C_{1-4}$ alkyl;
$R^{15}$ is hydrogen, $C_{1-4}$ alkyl or $B^1Q$;
$R^{16}$ is hydrogen or $C_{1-4}$ alkyl;
$B^1$ is a bond, or a straight or branched alkanediyl, alkylene oxaalkylene, or alkylene (oligooxalkylene) group, optionally containing one or more fluorine substituents; and
Q is a cationic or cationisable group of the formula —NR$^{17}_p$, —PR$^{17}_p$ and SR$^{17}_r$, in which p is 2 or 3, r is 1 or 2, the groups R$^{17}$ are the same or different and each is selected from the group consisting of hydrogen, $C_{1-24}$ alkyl and aryl, or two of the groups R$^{17}$ together with the heteroatom to which they are attached from a 5 to 7 membered heterocyclic ring or three R$^{17}$ groups together with the heteroatom to which they are attached form a 5 to 7 membered heteroaromatic ring, either of which rings may be fused to another 5 to 7 membered saturated or unsaturated ring, and any of the R$^{17}$ groups may be substituted by amino or hydroxyl groups or halogen atoms; wherein if p is 3, at least one of the groups R$^{17}$ is hydrogen.

Preferably $Y^1$ is $H_2C=CR^{14}$—CO-$A^8$- where $R^{14}$ is H or methyl and $A^8$ is O or NH. Preferred groups $B^1$ are alkanediyls, usually with linear alkyl chains and preferably having 2 to 12 carbon atoms, such as 2 or 3 carbon atoms.

Preferably Q is NR$^{17}_2$ where R$^{17}$ is $C_{1-12}$-alkyl. Preferably both R$^{17}$s are the same.

Particularly useful results have been achieved where the groups R$^{17}$ are $C_{1-4}$ alkyl, especially ethyl, methyl or isopropyl.

Either or both the hydrophobic and hydrophilic blocks of the second polymer may include comonomers, for instance to provide functionality, control over hydrophobicity, control over pH sensitivity, pKa or pKb as the case may be, control over temperature sensitivity or as general diluents. For instance comonomers providing functionality may be useful to provide conjugation of pendant groups following polymerisation and/or polymersome formation, to targeting moieties, or to provide for conjugation between the biologically active molecule and the polymer. Alternatively, functional groups may allow for crosslinking of the polymer following polymersome formation, to confer increased stability on the polymersome structure. Examples of suitable comonomers are compounds of the general formula (VIII)

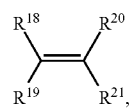

(VIII)

in which
$R^{18}$ is selected from hydrogen, halogen, $C_{1-4}$ alkyl and groups COOR$^{22}$ in which R$^{22}$ is hydrogen or $C_{1-4}$ alkyl;
$R^{19}$ is selected from hydrogen, halogen and $C_{1-4}$ alkyl;
$R^{20}$ is selected from hydrogen, halogen, $C_{1-4}$ alkyl and groups COOR$^{22}$ provided that R$^{18}$ and R$^{20}$ are not both COOR$^{22}$; and
$R^{21}$ is a $C_{1-10}$ alkyl, a $C_{1-20}$ alkoxycarbonyl, a mono- or di-($C_{1-10}$ alkyl)amino carbonyl, a $C_{6-20}$ aryl (including alkaryl) a $C_{7-20}$ aralkyl, a $C_{6-20}$ aryloxycarbonyl, a $C_{1-20}$-aralkyloxycarbonyl, a $C_{6-20}$ arylamino carbonyl, a $C_{7-20}$ aralkyl-amino, a hydroxyl or a $C_{2-10}$ acyloxy group, any of which may have one or more substituents selected from halogen atoms, alkoxy, oligo-alkoxy, aryloxy, acyloxy, acylamino, amine (including mono and di-alkyl amino and thalkylammonium in which the alkyl groups may be substituted), carboxyl, sulphonyl, phosphoryl, phosphino, (including mono- and di-alkyl phosphine and tri-alkylphosphonium), zwitterionic, hydroxyl groups, vinyloxycarbonyl and other vinylic or allylic substituents, and reactive silyl or silyloxy groups, such as trialkoxysilyl groups; or R$^{21}$ and R$^{20}$ or R$^{21}$ and R$^{19}$ may together form —CONR$^{23}$CO in which R$^{23}$ is a $C_{1-20}$ alkyl group.

It is preferred for at least two of the groups R$^{18}$, R$^{19}$, R$^{20}$ and R$^{21}$ to be halogen or, more preferably, hydrogen atoms. Preferably R$^{18}$ and R$^{19}$ are both hydrogen atoms. It is particularly preferred that compound of general formula X ia a styrene or acrylic compound. In styrene compounds R$^{21}$ represents an aryl group, especially a substituted aryl group in which the substituent is an amino alkyl group, a carboxylate or a sulphonate group. Where the comonomer is an acrylic type compound, R$^{21}$ is an alkoxycarbonyl, an alkyl amino carbonyl, or an aryloxy carbonyl group. Most preferably in such compounds R$^{21}$ is a $C_{1-20}$-alkoxy carbonyl group, optionally having a hydroxy substituent. Acrylic compounds are generally methacrylic in which case R$^{20}$ is methyl.

Preferably the comonomer is a non-ionic comonomer, such as a $C_{1-24}$ alkyl(alk)-acrylate or -acrylamide, mono- or di-hydroxy-$C_{1-6}$-alkyl(alk)-acrylate, or acrylamide, oligo ($C_{2-3}$ alkoxy) $C_{2-18}$-alkyl (alk)-acrylate, or -acrylamide, styrene, vinylacetate or N-vinyllactam.

For optimum nanovesicle formation, the block copolymers should have controlled molecular weights. It is preferable for each of the blocks to have molecular weight controlled within a narrow band, that is, to have a narrow polydispersity. The polydispersity of molecular weight should, for instance, be preferably less than 2.0, more preferably less than 1.5, for instance in the range 1.1 to 1.4. Of course, in the preferred embodiment wherein one of the blocks has a pKa in the range 3.0 to 6.9, the blocks should be selected so that they have the requisite pKa value.

In one embodiment of this invention, the monomer from which the hydrophobic block of the second polymer is formed is 2-(diisopropylamino)ethyl methacrylate (DPA) or 2-(diethylamino)ethyl methacrylate (DEA). In another embodiment, the hydrophilic block of the second polymer is PMPC or poly oligo (ethylene glycol) methacrylate (POEGMA). For example, the copolymer may be a PMPC-b-PDPA block copolymer or a POEGMA-PDPA block copolymer.

Preferably, the block copolymer has general formula $PMPC_m$-b-$PDPA_n$ or $POEGMA_m$-$PDPA_n$, wherein m is in the range 15-30 (for instance, 25) and n is 30 to 150, preferably 40 to 120, more preferably 60 to 80.

Typically, the hydrophobic block is not formed from 2-(dimethyl)ethyl methacrylate (DMA) monomers.

In another embodiment, the hydrophilic block of the second polymer is formed from ethylenically-unsaturated monomers that comprise a polyalkylene glycol side chain (e.g., a PEG side chain). For example, such monomers may comprise an ethylenic unsaturated group $H_2C=CR-CO-$ that is attached to the polyalkylene glycol side chain. Such acrylic moieties are preferably methacrylic, that is in which R is methyl, or acrylic, in which R is hydrogen. The polyalkylene glycol side chain may have the formula $-[O(CH_2)_n]_pOR_{24}$ in which n is from 1 to 6, p is from 1 to 100 and $R_{24}$ is hydrogen or $C_{1-6}$ alkyl. Preferably n is 2 (i.e., the side chain is a polyethylene glycol side chain). Preferably p is from 1 to 50, more preferably from 5 to 20. Preferably $R_{24}$ is hydrogen or methyl, most preferably hydrogen. It will be understood that individual molecules within such a monomer compound may have a distribution of molecular weights owing to a distribution in the extent of polymerisation in the side chain (i.e., a distribution in the value of p). Typical number average molecular weights of the monomers may be in the range 100 to 1000, preferably 200 to 800. A particularly preferred hydrophilic block of this nature is formed from oligo (ethylene glycol) methacrylate (OEGMA) monomers.

The block copolymer corresponding to the second polymer may be a simple A-B block copolymer, or may be an A-B-A or B-A-B block copolymer (where A is the hydrophilic block and B is the hydrophobic block). It may also be an A-B-C, A-C-B or B-A-C block copolymer, where C is a different type of block. C blocks may, for instance, comprise functional, e.g. cross-linking or ionic groups, to allow for reactions of the copolymer, for instance in the novel compositions. Crosslinking reactions especially of A-C—B type copolymers, may confer useful stability on polymersomes. Cross-linking may be covalent, or sometimes, electrostatic in nature. Cross-linking may involve addition of a separate reagent to link functional groups, such as using a difunctional alkylating agent to link two amino groups. The block copolymer may alternatively be a star type molecule with hydrophilic or hydrophobic core, or may be a comb polymer having a hydrophilic backbone (block) and hydrophobic pendant blocks or vice versa. Such polymers may be formed for instance by the random copolymerisation of monounsaturated macromers and monomers.

Further details of a suitable process for polymerising the monomers are to be found in WO 03/074090, the contents of which are herein incorporated by reference in their entirety. Living radical polymerisation process has been found to provide polymers of monomers having a polydispersity (of molecular weight) of less than 1.5, as judged by gel permeation chromatography. Polydispersities in the range 1.2 to 1.4 for the or each block are preferred. An advantage of the present invention where the hydrophobic block is pH sensitive, is that the polymersomes may be loaded using a pH change system. In such a process, polymer is dispersed in aqueous liquid in ionised form, in which it solubilises at relatively high concentrations without forming polymersomes. Subsequently the pH is changed such that some or all of the ionised groups become deprotonated so that they are in non-ionic form. At the second pH, the hydrophobicity of the block increases and polymersomes are formed spontaneously.

The first polymer may comprise a hydrophilic block that contains monomers as described above in connection with the hydrophilic block of the second polymer. The first polymer may comprise a hydrophobic block that contains monomers as described above in connection with the hydrophobic block of the second polymer. For example, the monomeric first polymer and the second polymer may differ only by way of the monomeric ratio of hydrophilic to hydrophobic monomers. Typically, though, at least the monomers in either the hydrophilic or the hydrophobic block of the first polymer (and often in both the hydrophilic and hydrophobic blocks) are different from the monomers in the corresponding block(s) of the second polymer.

One illustrative example of a first polymer is a copolymer based on poly(ethylene oxide) and poly(butylene oxide). Such copolymers are known to form polymersomes with very thin membranes (e.g. around 2.5 nm) of relatively high permeability to most small polar molecules. A specific example is a polymer of formula $PEO_a$-$PBO_b$, in which a is from 5 to 25 and b is from 10 to 30 (and preferably in which a is from 10 to 20 and b is from 15 to 25).

Other examples of first polymers include copolymers comprising any combination of (i) a hydrophobic PDPA or PBO block and (ii) a PEO or PMPC hydrophilic block.

As with the second polymer, the block copolymer corresponding to the first polymer may be a simple A-B block copolymer, or may be an A-B-A or B-A-B block copolymer (where A is the hydrophilic block and B is the hydrophobic block). It may also be an A-B-C, A-C-B or B-A-C block copolymer, where C is a different type of block. C blocks may, for instance, comprise functional, e.g. cross-linking or ionic groups, to allow for reactions of the copolymer, for instance in the novel compositions. Crosslinking reactions especially of A-C-B type copolymers, may confer useful stability on polymersomes. Cross-linking may be covalent, or sometimes, electrostatic in nature. Cross-linking may involve addition of a separate reagent to link functional groups, such as using a difunctional alkylating agent to link two amino groups. The block copolymer may alternatively be a star type molecule with hydrophilic or hydrophobic core, or may be a comb polymer having a hydrophilic backbone (block) and hydrophobic pendant blocks or vice versa. Such polymers may be formed for instance by the random copolymerisation of monounsaturated macromers and monomers.

A method of forming polymersomes with encapsulated drug and enzyme in the core wherein one of the blocks is pH-sensitive, may involve the following steps: (i) dispersing the amphiphilic copolymers (i.e. the first and second polymers) in an aqueous medium; (ii) acidifying the composition formed in step (i); (iii) adding the drug and enzyme to the acidified composition; and (iv) raising the pH to around neutral to encapsulate the drug and enzyme.

This method preferably comprises a preliminary step wherein the amphiphilic copolymers are dispersed in an organic solvent in a reaction vessel and the solvent is then evaporated to form a film on the inside of the reaction vessel.

By "pH-sensitive" is meant that one of the blocks has a group that becomes protonated/deprotonated at a particular pH. Preferably, one of the blocks, and typically a hydrophobic block comprises pendant groups which have a pKa in the range 3.0 to 6.9, for instance, 4.0 to 6.9. Step (ii), of acidifying the composition, typically reduces the pH to a value below the pKa of the pendant group.

In more detail, polymersomes are typically prepared by dissolving the copolymers in an organic solvent, such as a 2:1 chloroform:methanol mix in a glass container. Solvent can be evaporated under vacuum leaving a copolymeric film deposited on the walls of the container. The film is then re-hydrated with an aqueous solution, for instance using phosphate buffer saline. The pH of the resultant suspension is decreased to a pH of around 2, to solubilise the film, and then increased slowly to a pH or around 6. Once the pH has reached this value, enzyme and drug are typically added. The pH is then increased to around neutral, to encapsulate the drug and enzyme. The dispersion may then be sonicated and extruded, for instance using a bench top extruder. UV spectroscopy or HPLC chromatography may be used to calculate the encapsulation efficiency, using techniques well known in the art. An alternative method for forming polymersomes with encapsulated drug and enzyme may involve simple equilibration of the drug and enzyme vesicles in water. For instance drug and enzyme may be contacted in solid form with an aqueous dispersion of polymer vesicles and incubated, optionally with shaking, to solubilise the compounds in the dispersed vesicles. Alternatively, drug and enzyme in organic solvent may be emulsified into an aqueous dispersion of polymer vesicles, whereby solvent and drug and enzyme become incorporated into the core of the vesicles, followed by evaporation of solvent from the system. A preferred method for forming polymersomes encapsulating a drug and an enzyme is to use film rehydration. For instance, the drug and enzyme are solubilised in phosphate buffered saline (PBS) and placed in contact with the polymeric film obtained as described above. Over time the swelling of the polymeric film in the PBS/drug/enzyme solution generates loaded polymersomes. Alternatively, electroporation can be used to encapsulate the drug and the enzyme. In this case, pre-formed polymersomes are mixed with the drug and the enzyme and the solution is exposed to an electric filed. This temporarily creates pores in the polymersome membranes allowing the encapsulation of the drug and the enzyme.

For example, 0.01% to 10% (w/w) of drug may be mixed with copolymers in the methods described above.

Signalling Molecule, Enzyme and Product Molecules

The polymersome of the invention comprises an enzyme encapsulated within the polymersome. The enzyme is capable of converting a signalling molecule into one or more product molecules. Thus, chemotactic motion arises when the signalling molecule enters the polymersome, is converted by the enzyme to the one or more product molecules, and the product molecules then depart the polymersome in an asymmetric fashion caused by the asymmetric permeability of the polymersome to the product molecules.

The signalling molecule is typically a molecule that is present in vivo, for example in vivo in a human or animal, preferably a human. Usually the signalling molecule is present in the blood. The signalling molecule is capable of coming into contact, in vivo, with the polymersome after administration of the polymersome to the (e.g. human) subject.

The signalling molecule is typically a molecule of biological significance. For example, the signalling molecule may be a molecule that is present at an enhanced concentration in the vicinity of (e.g. at) a particular target tissue. Typically there exists a concentration gradient of the signalling molecule in vivo when measured in a direction of blood flow towards (or away from) the tissue of interest. The polymersome is capable of exhibiting chemotaxis along the concentration gradient as a result of the enzyme-catalysed reaction described herein.

The signalling molecule is typically a small molecule. For example, it may be easier to achieve the required permeability of the polymersome to the signalling molecule when the signalling molecule is a small molecule. Typically the signalling molecule has a molecular weight of 1000 Da or less, preferably 800 Da or less, more preferably 600 Da or less and most preferably 250 Da or less.

One exemplary signalling molecule is glucose. This sugar is critical for the metabolism of several tissues and the glucose gradient is highly controlled in several organs. Most notably, high metabolic active organs such as the brain require more glucose than other parts of our body with consequent over-expression of glucose transporters at the blood-brain barrier. Similarly, during oncogenesis, cancer cells increase their metabolic consumption of glucose, which creates localised glucose gradients within the tumour tissue and anomalous accumulation of glucose transporters in cancer cells. Further illustrative, and non-limiting, examples of signalling molecules include hydrogen peroxide (which may, for example, be present in enhanced concentrations near infection sites), lactate and fumarate (both of which may overexpressed by cancer cells), nitric oxide, and nucleosides such as nicotinamide adenine dinucleotide (NAD), adenosine triphosphate (ATP), adenosine diphosphate (ADP) and Adenosine monophosphate (AMP).

The enzyme encapsulated within the polymersome may be a single enzyme or a mixture of two or more enzymes. As will readily be understood, the choice of enzyme is determined by the signalling molecule of interest in any particular embodiment. For a given signalling molecule, an enzyme is chosen which has that signalling molecule as a substrate. Those skilled in the art would of course be well aware of the correlation between enzymes and their substrates (and thus the correlation between a particular enzyme and a particular signalling molecule).

Similar principles apply to the one or more product molecules. In particular, the identity of the one or more product molecules is determined directly by the identity of the signalling molecule and the enzyme.

For example, if the signalling molecule is glucose then a suitable enzyme is glucose oxidase. As is well known, glucose oxidase catalyses the conversion of glucose to d-glucono-6-lactone and hydrogen peroxide (i.e., one or more product molecules). The encapsulated enzyme may further comprise catalase. As is well known, catalase converts hydrogen peroxide to water and oxygen. Thus, a combination of glucose oxidase and catalase as the encapsulated enzyme is capable of converting glucose into d-glucono-☐-lactone, water and oxygen.

As a further example, if the signalling molecule is hydrogen peroxide then a suitable enzyme is catalase (the one or more products thus being water and oxygen).

It will of course be understood that other combinations of signalling molecule, enzyme and product molecules are possible and within the scope of this invention. What is essential is that the signalling molecule can be converted into one or more product molecules by the enzyme, the permeability of the polymersome to these one or more product molecules being different in the first and second regions of the polymersome.

Drug

The polymersome of the invention comprises a drug encapsulated within the polymersome. For the avoidance of doubt it is also possible to encapsulate a plurality of different drugs within a single polymersome, or to provide a plurality of polymersomes each containing a particular encapsulated drug.

As will be readily understood, the encapsulated drug is selected in accordance with the disorder to be treated. Non-limiting examples of such disorders are described elsewhere in this disclosure.

Non-limiting examples of drugs include: a drug that is effective for the treatment or prevention of a brain disorder; a drug that is effective for the treatment or prevention of the immune and/or inflammatory disorder; and a drug that is effective for the treatment or prevention of the cancer. There is no particular limitation on the identity of the drug and so drugs can be selected from those known in the art for treatment or prevention of the disorder of interest in any given embodiment.

Non-limiting examples of drugs include neuroprotectants, immunomodulatory drugs ("immunomodulators"), NSAIDs, corticosteroids, DMARDs, immunosuppressants, TNF-alpha inhibitors and anti-cancer drugs.

Illustrative and non-limiting examples of specific drugs that may be encapsulated include fumarate and fumarate esters, glutamate antagonists (e.g., Estrogen, Ginsenoside Rd, Progesterone, Simvastatin, Memantine), antioxidants (e.g., Acetylcysteine, Crocin, Fish oil, Minocycline, Pyrroloquinoline quinone (PQQ), Resveratrol, Vinpocetine, Vitamin E), Stimulants (e.g., Selegiline, Nicotine, Caffeine), Caspase inhibitors, Trophic factors (e.g., CNTF, IGF-1, VEGF, and BDNF), Anti protein aggregation agents (e.g. sodium 4-phenylbutyrate, trehalose, and polyQ-binding peptide), Erythropoietin, Lithium, carnosine, asiatic acid, flavonoids (e.g. xanthohumol, naringenin, galangin, fisetin and baicalin), cannabinoids (e.g., WIN55,212-2, JWH-133 and TAK-937), citicoline, minocycline, cerebrolysin, ginsenosoid-Rd, granulocyte-colony stimulating factor, Tat-NR2B9c, magnesium, albumin, paracetamol, aspirin, choline and magnesium salicylates, celecoxib, diclofenac (e.g. diclofenac potassium, diclofenac sodium), diflunisal, etodolac, fenoprofen, flurbiprofen, ibuprofen, indomethacin, ketoprofen, meclofenamate, mefenamic acid, meloxicam, nabumetone, naproxen (including naproxen sodium), oxaprozin, piroxicam, rofecoxib, salsalate, sodium salicylate, sulindac, tolmetin, valdecoxib, corticosteroids, alemtuzumab, interferon beta-lb, fingolimod, glatiramer acetate, natalizumab, plegridy, peginterferon beta 1a, teriflunomide, methotrexate, sulfasalazine, leflunomide, adalimumab, etanercept, golimumab, ustekinumab, azathioprine, cyclosporine, infliximab, golimumab, certolizumab, hydroxychloroquine, methotrexate, azathioprine, mycophenolate, acitretin, hydrea, isotretinoin, mycophenolate mofetil, sulfasalazine, 6-thioguanine, calcipotriol, calcitriol, tacalcitol, tacrolimus, pimecrolimus, dithranol, endamustine, bendamustine, carmustine, chlorambucil, cyclophosphamide, dacarbazine, ifosfamide, melphalan, procarbazine, streptozocin, temozolomide, capecitabine, 5-Fluoro Uracil, Fludarabine, Gemcitabin, Methotrexate, Pemetrexed, Raltitrexed, Actinomycin D, Bleomycin, Doxorubicin, Epirubicin, Mitomycin, Mitoxantrone, Etoposide, Docetaxel, Irinotecan, Paclitaxel, Topotecan, Vinblastine, Vincristine, Vinorelbine, Eribulin, Carboplatin, Cisplatin, Oxaliplatin, Afatinib, Aflibercept, BCG, Bevacizumab, Brentuximab, Cetuximab, Crizotinib, Denosumab, Erlotinib, Gefitinib, Imatinib, Interferon, Ipilimumab, Lapatinib, Panitumumab, Pertuzumab, Rituximab, Sunitinib, Sorafenib, Trastuzumab emtansine, Temsirolimus, Trastuzumab, Vemurafenib, Clodronate, Ibandronic acid, Pamidronate, Zolendronic acid, Anastrozole, Abiraterone, Bexarotene, Bicalutamide, Buserelin, Cyproterone, Degarelix, Exemestane, Flutamide, Folinic acid, Fulvestrant, Goserelin, Lanreotide, Lenalidomide, Letrozole, Leuprorelin, Medroxyprogesterone, Megestrol, Mesna, Octreotide, Stilboestrol, Tamoxifen and Thalidomide.

Targeting Moiety

The polymersome preferably comprises a targeting moiety on its external surface. By on its external surface is meant that the targeting moiety is located such that it is able to interact with its target (as opposed to being located at an inaccessible position that precludes interaction with the target, for example by being encapsulated within the polymersome).

The targeting moiety is adapted to enable the polymersome to bind to a target. Typically the targeting moiety binds selectively to the target. The target is a chemical substance that is located on or in the vicinity of the tissue of interest (and thus enables the polymersome to be accumulate specifically at the tissue of interest in preference to other sites). The target is preferably a receptor, e.g. a receptor that is present in particularly high quantity at the target tissue of interest.

The targeting moiety can be any moiety that binds specifically to the target. As is well known in the art, for example from the well developed field of bioconjugates, a wide range of substances can be used as targeting moieties, e.g. to target receptors.

In one embodiment, the targeting moiety is a moiety that is attached to the external surface of the polymersome. Examples of suitable targeting moieties include antibodies, antibody fragments, aptamers, oligonucleotides, small molecules, peptides and carbohydrates. Peptide, antibody and antibody fragment targeting moieties are particularly preferred. However, any such moiety can be used as a targeting moiety in the present invention. The suitability of any given moiety to target any given receptor can be determined using routine assay methods, involving testing for the ability of the moiety to bind specifically to the receptor.

One example of a targeting moiety is a targeting moiety that is adapted to enable the polymersome to cross the blood-brain barrier (BBB). This property of the targeting moiety arises through the ability of the targeting moiety to bind to a target (e.g. a receptor) at the blood-brain barrier, wherein the target (e.g. receptor) mediates transcytosis across the blood-brain barrier.

Examples of receptors for receptor-mediated transcytosis that are highly expressed on the endothelial cells that form the blood-brain barrier include low-density lipoprotein receptor-related protein 1 (LRP-1), insulin receptor (IR) and transferrin receptor (TfR), all of which are suitable targets for the targeting moiety.

Preferably, however, such a targeting moiety targets the LRP-1 receptor. LRP1 is a member of the LDL receptor family that plays diverse roles in various biological processes including lipoprotein metabolism, degradation of proteases, activation of lysosomal enzymes and cellular entry of bacterial toxins and viruses. Deletion of the LRP1 gene leads to lethality in mice, revealing a critical, but as of yet, undefined role in development. Tissue-specific gene deletion studies reveal an important contribution of LRP1 in the vasculature, central nervous system, in macrophages and in adipocytes. Three important properties of LRP1 dictate its diverse role in physiology: first, its ability to recognise more than thirty distinct ligands; second, its ability to bind a large number of cytoplasmic adaptor proteins via determinants located on its cytoplasmic domain in a phosphorylation-specific manner; and third, its ability to associate with and modulate the activity of other transmembrane receptors such as integrins and receptor tyrosine kinases.

It has been found that provision of a polymersome that features a targeting moiety that targets the LRP1 receptor enables the polymersome both to cross the BBB and to deliver efficiently an encapsulated drug into both the CNS parenchyma and CNS cells. In particular, it has been found that the endothelial transcytosis mechanism does not involve acidification of the polymersome in membrane-trafficking organelles, which is important to avoid premature distintegration of the polymersome and concomitant release of the encapsulated drug. Still further, the LRP1 receptor is associated with traditional endocytosis in CNS cells, which, subsequent to navigation across the BBB, aids the delivery of the drug within their cytosol (via disintegration of the polymersome). In particular, providing a targeting moiety that targets the LRP1 receptor has been found to enable the polymersome to achieve efficient neuroprotectant effects in the treatment of stroke.

Peptides that bind to the receptor LRP1 are known in the art. For example, Angiochem (Montreal, Canada) have developed peptides that the leverage the LRP-1 mediated pathway to cross the blood-brain barrier when conjugated to drug cargos. One specific example of a peptide that is suitable for use in the present invention is Angiopep-2, which is a peptide having the sequence TFFYGGSRGKRNNFKTEEY (SEQ ID NO: 1). Further examples of suitable targeting moieties are disclosed in WO 2013/078562, the contents of which are herein incorporated by reference in their entirety (and, specifically, the targeting moiety peptides disclosed in which are herein incorporated by reference).

Another example of a targeting moiety is a targeting moiety that is adapted to enable the polymersome to bind to a cancer cell. Illustrative and non-limiting examples of such targeting moieties include proteins (mainly antibodies and their fragments), peptides, nucleic acids (aptamers), small molecules, vitamins and carbohydrates.

A further example of a targeting moiety is a targeting moiety that is adapted to enable the polymersome to bind to an immune cell. Illustrative and non-limiting examples of such targeting moieties include phosphorylcholine (as discussed in more detail below), peptidoglycan, lipoproteins, glycolipids, lipopolysaccharide, lipopeptides, synthetic compounds such as loxoribine and bropirimine, peptidoglycans, acetylated/malelylated proteins, modified low-density lipoproteins, polyanionic ligands, sulfated sugars, mannose-modified polysaccharides, fucose-modified polysaccharides, galactose-modified polysaccharides, proteins and β-glucan.

The targeting moiety can be attached to the external surface of the polymersome using routine techniques, for example by adapting well known methods for attaching targeting moieties to polymers, drugs, nucleic acids, antibodies and other substances. The attachment may be non-covalent (e.g. electrostatic) or covalent, though it is preferably covalent. For example, the targeting moiety can be attached by reacting a suitable functional group on the targeting moiety (including but not limited to an amine group, a carboxyl group and a thiol group) with a corresponding functional group on at least one of the copolymers that form, or will form, the polymersome. The attachment can be effected either before the polymersome structure is formed from the copolymers, or after the polymersomes have been formed.

It is also possible to provide for attachment of the targeting moiety to the copolymers by first chemically activating either or both of the targeting moiety and the copolymers. For example, a peptide targeting moiety may be activated by adding a reactive species to one of its termini, such as a cysteine moiety (whose thiol group is well known to react readily with functional groups such as the widely used maleimide moiety). Similarly, a copolymer can be activated by functionalising it with a reactive species (e.g. a maleimide moiety when the targeting moiety carries a thiol group). The copolymer may be provided with such a reactive species either by functionalisation of the copolymer itself, or by providing suitable monomers prior to the polymerisation that forms the copolymer, or by providing a suitable initiator for the polymerisation.

The targeting moiety may be attached directly to the external surface of the polymersome or it may be attached via a chemical spacer.

The targeting moiety may also be a pendant group of a polymer comprised by the polymersome (i.e. at least one of the copolymers forming the polymersome itself). Clearly in this embodiment it is not necessary to undertake separate synthetic steps to attach the targeting moiety to the copolymer or the resulting polymersome.

Suitable pendant groups generally include any group that corresponds to a targeting moiety as defined elsewhere herein. In one illustrative embodiment, the targeting moiety is a phosphorylcholine moiety, i.e. a group having the formula

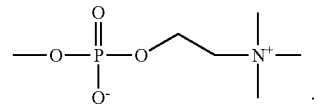

A phosphorylcholine moiety is a zwitterionic moiety that can constitute a pendant group in one or more of the monomers that form the copolymers comprised in the polymersome. For example, the phosphorylcholine moiety corresponds to a group of formula (III) as defined herein, wherein m is 2 and each $R^5$ is methyl. The illustrative hydrophilic block PMPC comprises phosphorylcholine moieties.

The phosphorylcholine moiety selectively targets scavenger receptor B1 over-expressed by macrophages and other immune cells; in particular it enables a polymersome featuring phosphorylcholine moieties to enter such cells. Thus, polymersomes featuring a phosphorylcholine targeting moiety are particularly suitable for use in the treatment of inflammatory and/or immune disorders.

Pharmaceutical Composition

The polymersome of the present invention can be formulated as a pharmaceutical composition using routine techniques known in the art. For example, pharmaceutical compositions already utilised for the formulation of polymersomes or drug-containing liposomes.

The pharmaceutical composition comprises a plurality of the polymersomes of the present invention. It also comprises one or more pharmaceutically acceptable excipients or diluents. The one or more pharmaceutically acceptable excipients or diluents may be any suitable excipients or diluents. The pharmaceutical composition is typically aqueous, i.e. it contains water (in particular sterile water).

A typical pH of the aqueous pharmaceutical composition is 7.0 to 7.6, preferably 7.2 to 7.4.

Pharmaceutically acceptable buffers may be used to achieve the required pH. The pharmaceutical composition may be in the form of a sterile, aqueous, isotonic saline solutions.

Typically the pharmaceutical composition is an injectable composition, e.g. it is suitable for intravenous delivery, for example it is suitable for infusion.

Medical Uses of the Polymersomes

The polymersomes of the present invention are able to target tissues including, but not limited to cells (e.g. CNS cells) beyond the blood-brain barrier, immune cells and cancer cells and to release drugs once localised at the target. The high efficiency in targeting may emerge, in part, through the presence of targeting moieties comprised by the polymersome (e.g. as part of the polymers themselves or as distinct moieties attached thereto). However, the high efficiency in targeting also arises at least in part as a result of the chemotactic motion of the polymersomes, which overcomes conventional diffusion limitations and provides for a high degree of interaction of the polymersomes with desired receptors.

Thus, the polymersomes can be used in methods for the improved targeted treatment of diseases and other pathological conditions.

As will be readily understood, a targeting moiety and encapsulated drug are selected in accordance with the disease to be treated. For example, if the disorder is a brain disorder then the targeting moiety may be a targeting moiety that is adapted to enable the polymersome to cross the BBB and, typically, enter cells such as CNS cells beyond the BBB, while the drug is a drug that is effective for the treatment or prevention of the brain disorder. If the disorder is an immune and/or inflammatory disorder then the targeting moiety may be a targeting moiety that is adapted to enable the polymersome to bind to (and typically enter) an immune cell, while the drug is a drug that is effective for the treatment or prevention of the immune and/or inflammatory disorder. If the disorder is a cancer then the targeting moiety may be a targeting moiety that is adapted to enable the polymersome to bind to (and typically enter) a cancer cell, while the drug is a drug that is effective for the treatment or prevention of the cancer.

Examples of brain disorders include stroke, neurodegenerative diseases, traumatic brain injury (TBS), spinal cord injury, and neurotoxin consumption (for example, methamphetamine overdoses). Neurodegenerative diseases include conditions such as amyotrophic lateral sclerosis, Parkinson's disease, Alzheimer's disease and Huntington's disease. Stroke may be ischemic stroke or haemorrhagic stroke.

Examples of immune and/or inflammatory disorders include multiple sclerosis, psoriatic arthritis, rheumatoid arthritis, lupus erythematosus and psoriasis.

Examples of cancers include: cancers of the skin, such as melanoma; lymph node; breast; cervix; uterus; gastrointestinal tract; lung; ovary; prostate; colon; rectum; mouth; brain; head and neck; throat; testes; thyroid; kidney; pancreas; bone; spleen; liver; bladder; larynx; nasal passages; AIDS-related cancers; cancers of the blood and bone marrow, such as multiple myeloma and acute and chronic leukemias, for example, lymphoblastic, myelogenous, lymphocytic, and myelocytic leukemias; advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, chronic lymphocytic leukemia (CLL), Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, eiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

Further disorders that may be susceptible to treatment or prevention with the polymersomes of the invention include HIV, atherosclerosis, ischemic heart disease and obstructive sleep apnoea.

Medical uses and methods of treatment, of course, involve the administration of a therapeutically effective amount of the polymersome. A therapeutically effective amount of the polymersomes is administered to a patient. A typical dose is from 0.001 to 1000 mg, measured as a weight of the drug, according to the activity of the specific drug, the age, weight and conditions of the subject to be treated, the type and severity of the disease and the frequency and route of administration. Preferably, daily dosage levels are from 0.001 mg to 4000 mg.

The present invention further provides a method of treating or preventing a disorder that comprises administering a therapeutically effective amount polymersome of the invention to a patient in need thereof. For example, the is a method of treating or preventing a disorder selected from any disorder specified in this disclosure, the drug being a drug that is capable of treating or preventing the said disorder. The present invention still further provides the use of a polymersome of the present invention in the manufacture of a medicament for use in a method of treating or preventing a disorder as identified above.

EXAMPLES

Example 1: Demonstration of Chemotaxis In Vitro

Figure 2A:
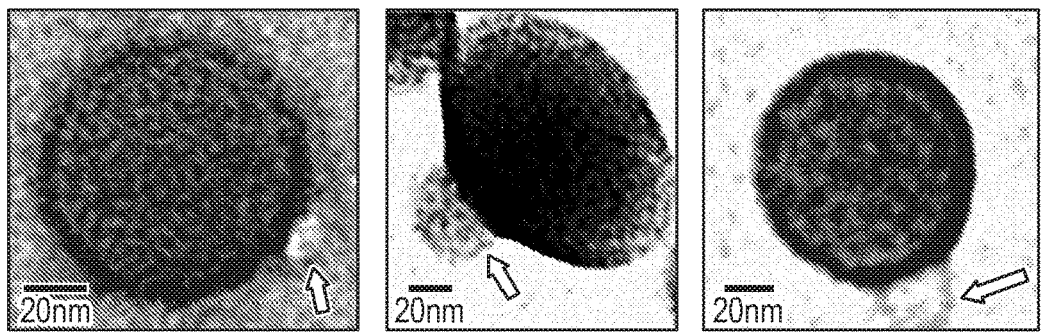
FIG. 2 shows (A) TEM images obtained for asymmetric 90/10 PMPC/PEO polymersomes and (B) a schematic representation of a chemotactic polymersome using a combination of membrane topology engineering and enzyme encapsulation.

The chemotactic effect has been exploited using two very different copolymers: poly((2-methacryloyl)ethyl phosphorylcholine)-poly(2-(diisopropylamino)ethyl methacrylate) (denoted PMPC25-PDPA70) and poly(ethylene oxide)-poly(butylene oxide) (denoted PEO11-PBO22). These two copolymers have very different molecular weights and chemical compositions, hence they assemble to form membranes with differing thicknesses and permeabilities. In particular, $PEO_{11}$-$PBO_{22}$ forms a very thin membrane (~2.5 nm) of relatively high permeability to most small polar molecules. The two copolymers form asymmetric polymersomes at a 9:1 PMPC-PDPA:PEO-PBO molar ratio (90/10 PMPC/PEO) with the small permeable bud being formed by the minor PEO-PBO component. In FIG. 2A Transmission Electron Microscopy (TEM) studies reveal such a structure when using selective staining for the PMPC-PDPA component.

Figure 2B:
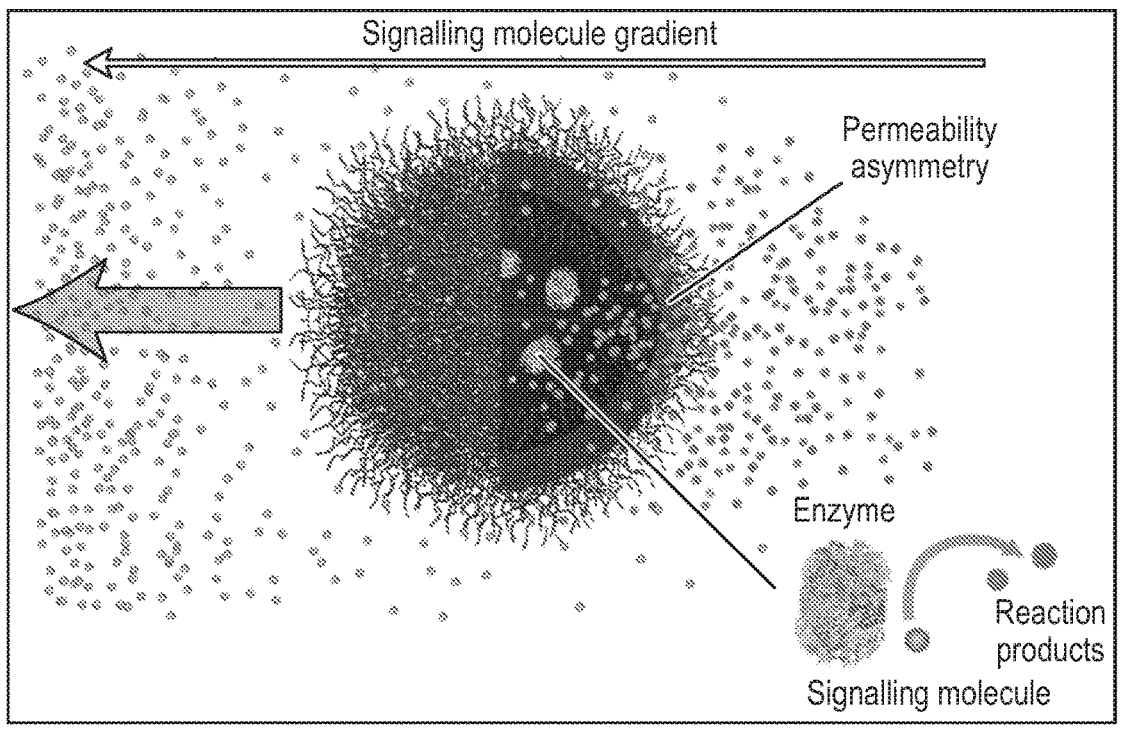

As schematised in FIG. 2B, if suitable enzymes are encapsulated within such asymmetric polymersomes, they can convert a given signalling molecule into products which will be expelled via the more permeable patch. This generates an asymmetric flux of chemicals, which it is hypothesised will lead to the propulsion of the polymersomes via self-diffusiophoresis and self-osmophoresis. The actual direction of propulsion could possibly be both towards or away from the permeable patch, depending on the interplay between the gradient caused by the depletion of the signalling molecule, the opposite gradient cause by the product release, and the relative strength of the interaction between the different molecules and the polymersome surface. An important condition for motility is that the signalling/fuel molecule penetrates the polymersome membrane relatively easily to reach the isolated enzyme. Thus hydrogen peroxide and glucose were chosen as fuel in this Examples and catalase and glucose oxidase as the encapsulated enzymes. Catalase catalyses the decomposition of hydrogen peroxide into water and oxygen while glucose oxidase catalyses glucose oxidation to form d-glucono-δ-lactone and hydrogen peroxide.

To characterise the diffusion behaviour of asymmetric polymersomes, a technique known as Nanoparticle Tracking Analysis (NTA) has been employed. This is based on the imaging the scattered light of nanoparticles illuminated by monochromatic laser using a fast camera and software recognition that tracks each particle individually. The trajectories and the consequent mean square displacements (MSD) can thus be used to extract propulsion velocities and diffusion coefficients (that can be related to particle size when there is no activity). NTA allows the simultaneous measurements of thousands of nanoparticle tracks, enabling the Brownian dynamics of given particle populations to be probed with temporal resolution of 30 frames per second. In FIG. 3 we show the data obtained for different combinations of encapsulated enzymes and substrate concentration gradients. The latter is achieved by adding a given concentration from one side of the observation chamber. The data displaying the nanoparticle tracks was plotted from 0 s to 0.5 s normalising their absolute displacement for an arbitrary origin. These displacements and consequent tracks can be further analysed by calculating the respective mean square displacement MSD.

The data obtained for catalase-loaded 90/10 polymersome diffusion as a function of the hydrogen peroxide concentration gradient are shown in FIG. 3A. As the concentration of hydrogen peroxide increases, the polymersome population displacements begin to polarise toward the hydrogen peroxide gradient (the orientation of which is shown by the arrow). Given the typical radius of around 50 nm (FIG. 3A), it is to be expected for the polymersomes to randomise their orientations in around 0.4 ms due to rotational diffusion. A population of the polymersomes follow trajectories that exhibit orientation persistence up to 10000 times longer than the time scale of rotational diffusion, which suggests that the external hydrogen peroxide (fuel) gradient can rectify the stochastic motion of the self-propelled systems, in accordance with recent theoretical predictions. Similar results can be observed by plotting the total particle MSD at 0.5 s and the angle of displacement between the origin and the final position. In addition to this, the particles' diffusional regimes can be assessed by the MSD plots. If the particle moves according to a random walk, the MSD changes linearly with time. This is the behaviour observed for the asymmetric polymersomes without hydrogen peroxide as well as the symmetric or empty polymersomes. As the hydrogen peroxide concentration is increased, several particle tracks exhibit non-linear MSDs, which are typical of the ballistic regime and are characteristic of self-propulsion. At higher hydrogen peroxide concentrations, deviations from linearity become more pronounced. Such behaviour can be summarised by gating all the MSD tracks relative to their control (i.e. zero hydrogen peroxide concentration) and calculating the MSD at an arbitrary time of 0.5 s. From the control-gated MSDs averaged over three independent measurements as a function of the signalling molecule concentration, it is evident that the propensity for directed self-propulsion increases with hydrogen peroxide gradient.

The apparent drift velocity VD of the polymersomes at the long time scale of observation can be calculated as:

$$V_D = \left(\mu_0 + \frac{\mu_1 V_0}{4D_r R}\right) \nabla C \quad (1)$$

in terms of the zeroth $\mu_0$ and first $\mu_1$ Legendre polynomial harmonic of the diffusiophoretic mobility, the propulsion velocity $V_0$, the rotational diffusion coefficient $D_r$, the particle radius R, and the concentration gradient of the signalling molecule ∇C. The factor $\mu_1 \nabla C/4D_r R$ gives the degree of alignment or polarisation of the asymmetric (and hence self-propelled) polymersomes. Using typical estimates for the parameters, it is found that an alignment factor of order unity is possible for concentrations of around 100 mM and above. The propulsion efficiency is not simply proportional to the hydrogen peroxide concentration and is showing alignment at concentrations much lower than 100 mM. This may be because of the effect of the injection process on the distribution of the dissolved hydrogen peroxide. Moreover, the permeability of both the hydrogen peroxide fuel and its oxygen and water by-products across the polymersome membranes could influence the self-propulsion mechanism.

To examine the universality of this approach glucose oxidase were also encapsulated within the 90/10 polymersomes and added glucose fuel to the solution. This enzyme catalyses glucose oxidation to form d-glucono-δ-lactone and hydrogen peroxide. Thus, the signalling molecule, the enzyme and its reaction products are completely different from the catalase formulation discussed above. The NTA for such a system (see FIG. 3B) reveals that Glucose oxidase-loaded asymmetric polymersomes also exhibit self-propulsion behaviour with a large displacement at 0.5 s and non-linear MSD trends. However, self-propulsion is only displayed at relatively high glucose gradients (~1M). At lower gradients, although the control-gated average MSD at 0.5 s shows some minimal increase in the total displacement, the majority of the particles are not aligned nor self-propelled. Although this glucose oxidase formulation is less sensitive towards its signalling molecule concentration these data confirm that self-propulsion can be achieved by confining an enzymatic reaction within an asymmetric polymersome. Moreover, the glucose oxidase propulsion efficiency can be considerably increased by co-encapsulating catalase within the same polymersome. Notably, one of the products of glucose oxidation is hydrogen peroxide, which is a substrate for the catalase reaction. Such a cascade system leads to the total conversion of one molecule of glucose to produce three molecules (d-glucono-δ-lactone, water and oxygen). As shown in FIG. 3C, the combination of the two enzymes significantly increases the self-propulsion efficiency of the polymersomes, with greater average displacement being observed at glucose gradients as low as 1 pM. It is expected that the two-enzyme polymersome will be much more efficient in self-propulsion.

Figure 4C:
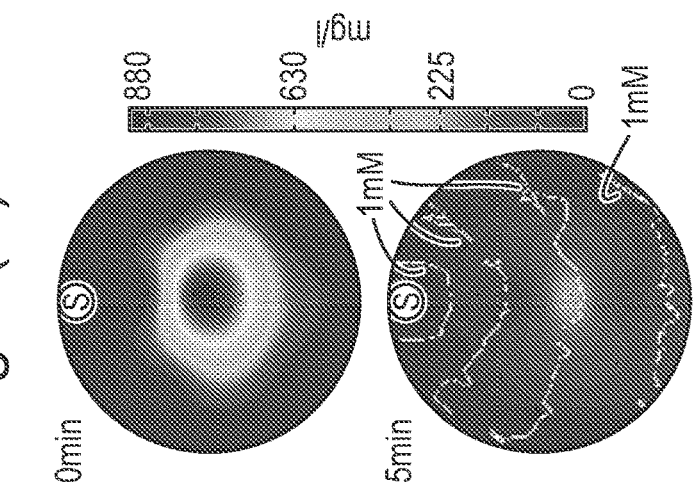
FIG. 4 shows collective chemotaxis analysis. (A) Schematic representation of the Petri dish set-up used to assess polymersome chemotaxis. 2D mapping of the Petri dish as a function of polymersome concentration at time 0 and 5 minutes after addition for catalase and glucose oxidase-loaded symmetric 100% PMPC polymersomes exposed to a glucose gradient (B), empty asymmetric 90/10 PMPC/PEO polymersomes exposed to a glucose gradient (C), catalase-loaded asymmetric 90/10 PMPC/PEO polymersomes exposed to a hydrogen peroxide gradient (D), and glucose oxidase-loaded asymmetric 90/10 PMPC/PEO polymersomes exposed to a glucose gradient (E), and glucose oxidase and Catalase-loaded asymmetric 90/10 PMPC/PEO polymersomes exposed to a glucose gradient (F). Note that the S denotes the substrate releasing gel. Substrate gradients, at 5 minutes, are plotted as superimposed isocratic curves (white lines) that have been calculated using computational fluid dynamic software.
Figure 4B:
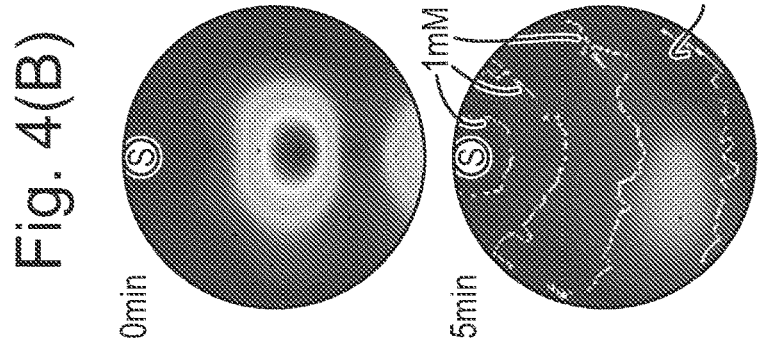
Figure 4A:
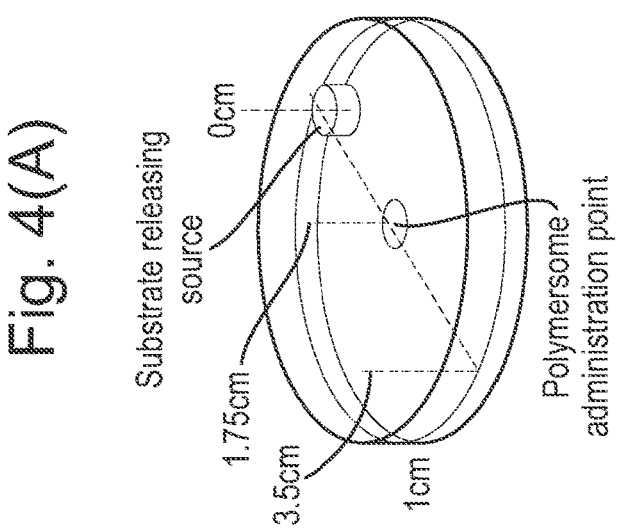
Figure 4D:
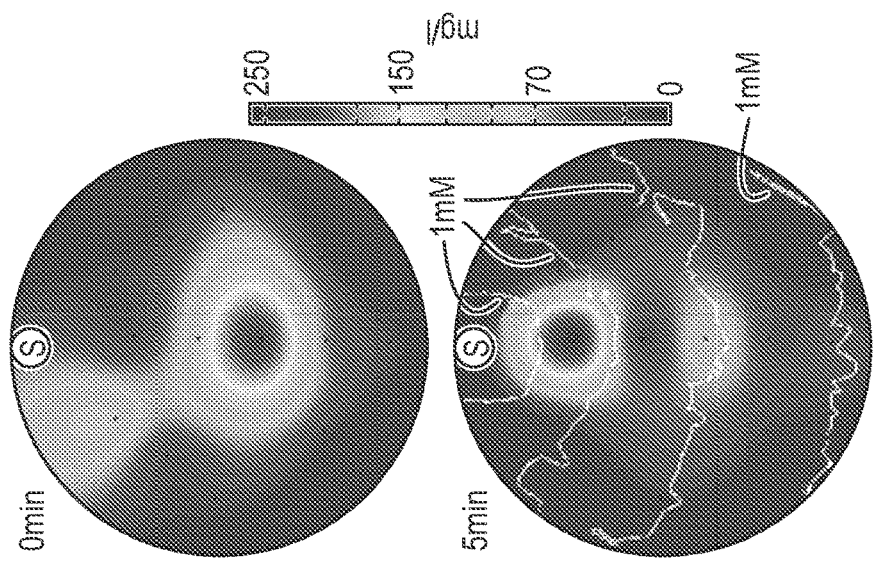
Figure 4E:
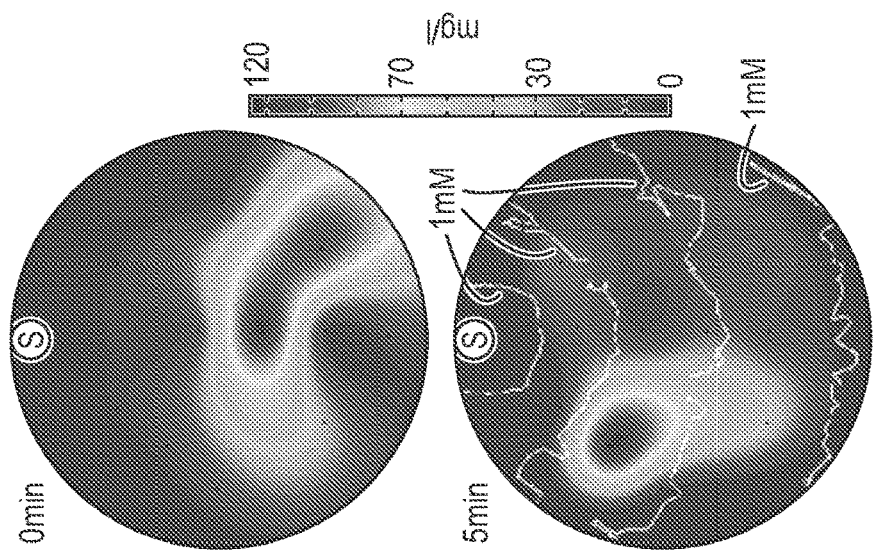
Figure 4F:
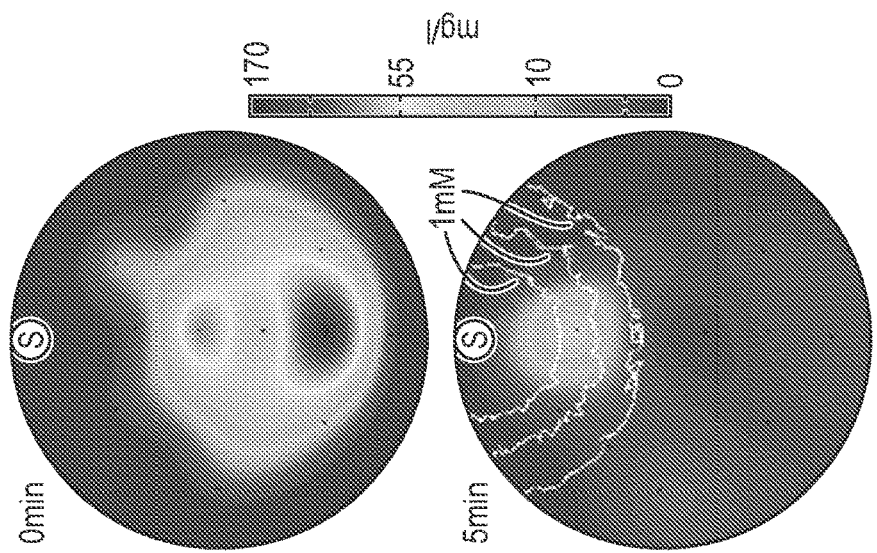

In addition to the NTA analysis, quantitative chemotaxis assessment was also performed using the system schematised in FIG. 4A. A cylindrical agarose gel pre-soaked in hydrogen peroxide (c.a. 1M) or glucose (c.a 10M) is placed on the edge of a Petri dish filled with Phosphate Buffer Solution (PBS). Various polymersome formulations were added at the centre of the dish using a syringe pump. Samples were collected at different locations within the Petri dish at different time points and quantified by NTA for concentration and size analysis. FIG. 4B shows the dish polymersome concentration heat maps at time 0 and 5 mins after polymersome addition for the 100% PMPC-PDPA symmetric formulation loaded with Catalase and Glucose oxidase exposed to a glucose gradient. FIG. 4C shows the heat maps for the empty 90/10 PMPC-PDPA/PEO-PBO asymmetric polymersomes also exposed to a glucose gradient. For both formulations, the diffusion follows an expected random distribution with an unbiased dilution effect. On the contrary the heat maps for 90/10 PMPC-PDPA/PEO-PBO asymmetric polymersomes loaded with catalase and exposed to a hydrogen peroxide gradient (FIG. 4D) and loaded with glucose oxidases (FIG. 4E) and glucose oxidase and catalase (FIG. 4F) exposed to a glucose gradient show a very different outcome. The asymmetric polymersomes show a clear biased distribution of the polymersomes toward the signalling molecule source. As for the single particle analysis, the collective chemotactic behaviour is also considerably more efficient for the cascade system where the two enzymes are combined within the same polymersome. More importantly, this experiment shows quite convincingly that the chemotactic polymersomes can follow shallow gradients and concentrate toward a given chemical source over considerably longer time scales.

In conclusion, it has been demonstrated that the encapsulation of suitable enzymes within asymmetric polymersomes enables their self-propulsion toward the enzyme substrate. The judicious combination of enzyme reactivity and membrane topology allows for self-propulsion and chemotaxis. This has been shown using two different substrates hydrogen peroxide and glucose.

The invention allows nanoscopic carriers to be engineered that can detect and target small molecule gradients over distances that are many orders of magnitude greater than the particle length scale. This concept has implications for targeted drug delivery, as well as for designing new chemical sensors, catalysis, and possibly even energy conversion. This provides a new paradigm in chemotaxis by showing that this is possible at significantly shorter length scales than the micron length scales utilised by living systems.

Example 2: Demonstration of Selective Tissue Targeting In Vivo

Materials (Poly [oligo(ethylene glycol) methyl methacrylate] poly (2-(diisopropylamino)ethyl methacrylate) (POEGMA-PDPA) and Rhodamine 6G-POEGMA-PDPA were synthesised by ATRP. Poly(ethylene oxide)-block-poly(butylene oxide) (PEO16-PBO22) (Mw=1910 Da) was synthesised via ATRP. Sepharose 4B, dextran mw 64-74000, D-glucose, glucose oxidase from *A. niger* and catalase from bovine liver were purchased from Sigma-Aldrich UK (Poole, Dorset, UK). Phosphate buffered saline (PBS) was obtained from Oxoid Ltd. Sodium hydroxide and Fisherbrand™ Electroporation Cuvettes Plus™ were purchased from Fischer Scientific (UK) and hydrochloric acid from BHD AnalR (UK).

Polymersome Preparation and Physicochemical Characterisation Thin copolymer films were made in the blends of P(OEG10)MA20-PDPA100 only, 1.2% (mol) Angiopep-2-P(OEG10)MA20-PDPA100, or 90% (1.2% (mol) Angiopep-POEGMA-PDPA)-10% PEO16-PBO22. All polymer films were fluorescently labelled by including 20% (mol) rhodamine 6G-POEGMA-PDPA. Film rehydration in pH 7.4 PBS occurred over 14 days at 25° C. to form polymersomes. Polymersomes were purified from aggregates and micelles via gel permeation chromatography (GPC) using sepharose 4B as a substrate. Polymersome and protein solutions (5 mg/ml and 1 mg/ml, respectively) were loaded into electroporation cuvettes and encapsulated using an Eppendorf 2510 electroporator at 2500V for a total of 10 pulses followed by GPC purification to remove residual free protein.

Dynamic light scattering (DLS) was used to assess the size distribution of polymersomes, via a Malvern Zetasizer Nano ZS laser light scatterer equipped with a He-Ne 4 mW 633 nm laser. Polymersomes were diluted in filtered PBS in 1 ml disposable cuvettes, and experiments were an average of n=3 runs at a set angle of 173°. Polymersomes in filtered PBS were also assessed for morphology using transmission electron microscopy (TEM). Samples were mounted on glow-discharged carbon coated grids by submerging the grids into the polymersome solution for 60 seconds, followed by staining for 5 seconds using 0.75% (w/w) phosphotungstic acid (PTA). Grids were then washed with PBS, dried under vacuum and assessed via a JEOL microscope using 100 kV voltage tension.

Nanosight Nanoparticle Tracking Analysis (NTA)

Polymersomes were diluted approximately 1:10000 in filtered PBS and injected into a Nanosight LM10 microscope. All experiments were performed under heating to 37° C. 60 second videos of 30 fps were captured via a sCMOS CCD camera, with glucose of varying concentrations or PBS was injected to the sample chamber full of polymersomes. Post-acquisition analysis via Nanosight NTA 2.3 software yields the exact coordinates and diffusion coefficient of all the nanoparticles visible in the sample chamber. This data was further processed by MATLAB. The MATLAB code yielded the mean squared displacement (MSD) of all particles analysed, as well as a visualisation of all trajectories and their coordinates.

Brain In Situ Perfusion

All animal experiments were performed in accordance with the Animals (Scientific Procedures) Act 1986 (U.K.). Male adult Wistar rats were anaesthetised with 100 mg/kg ketamine and 1 mg/ml medetomidine via intraperitoneal injection. The right and left external carotid arteries were isolated from the carotid sheaths and cannulated according to a previously established procedure. The perfusion fluid was bubbled with 5% $CO_2$ and heated to 37° C. for 20 minutes prior to perfusion. The perfusate consisted of 90% modified Ringer's solution (6.896 g/L NaCl, 0.350 g/L KCl, 0.368 g/L $CaCl_2$, 0.296 g/L $MgSO_4$, 2.1 g/L $NaHCO_3$, 0.163 g/L $KH_2SO_4$, 2.383 g/L HEPES, additionally 0.5005 g/L glucose (5.5 mM) and 11.1 g/L BSA), the remaining 10% of approx. 1 mg/ml polymersomes in Krebs buffer (pH 7.4, 188 mM NaCl, 4.7 mM KCl, 2.5 mM CaCl2, 1.2 mM MgSO4, 1.2 mM KH2PO4, 25 mM $NaHCO_3$, 10 mM D-glucose, 3 g/dl BSA). The polymersome solution was supplied via syringe pump at 0.16 ml/min, with a total perfusion rate of 1.5 ml/min. At the end of the perfusion time, the syringe pump was stopped and the arteries were flushed for 60 seconds with modified Ringer's perfusate in order to remove unbound polymersomes, followed by immediate extraction of cerebrospinal fluid via cisternal puncture followed by decapitation and removal of the brain.

Quantification of Polymersome Distribution in the Rat Brain

After decapitation, brains were removed and washed in ice cold 9 g/L NaCl, followed immediately by homogenisation on ice. Briefly, the cerebellum was removed and the brain was weighed, adding 2× brain weight in PBS followed by 3× dilution in 30% (w/v) dextran (average mw 64-74 k). Centrifugation of homogenates at 7400 g for 20 minutes in 4° C. resulted in several fractions that were carefully separated: capillary depleted (CD) fraction (i.e. parenchyma), dextran, and the capillary enriched fraction (pellet). The capillary enriched pellet was re-suspended in PBS, and 100 µl samples were added to a black 96-wellplate and read in a fluorimeter at an excitation wavelength of 540 nm and emission at 565 nm.

All sample fluorescence readings were normalised to sham readings for each sample type, i.e. CD, dextran or capillaries. Positive controls were polymersomes in perfusate harvested from the cannula at the injection point. Normalised fluorescence readings were converted to polymersome (rhodamine) amount was converted into % injected dose % id of the positive control value for that experiment, where % id=[normalised sample value (mg)÷mean positive control value (mg)]*100. This was further converted into fluorescence per whole brain. All statistical analysis was one-way ANOVA, $p<0.05$.

Figure 5A:
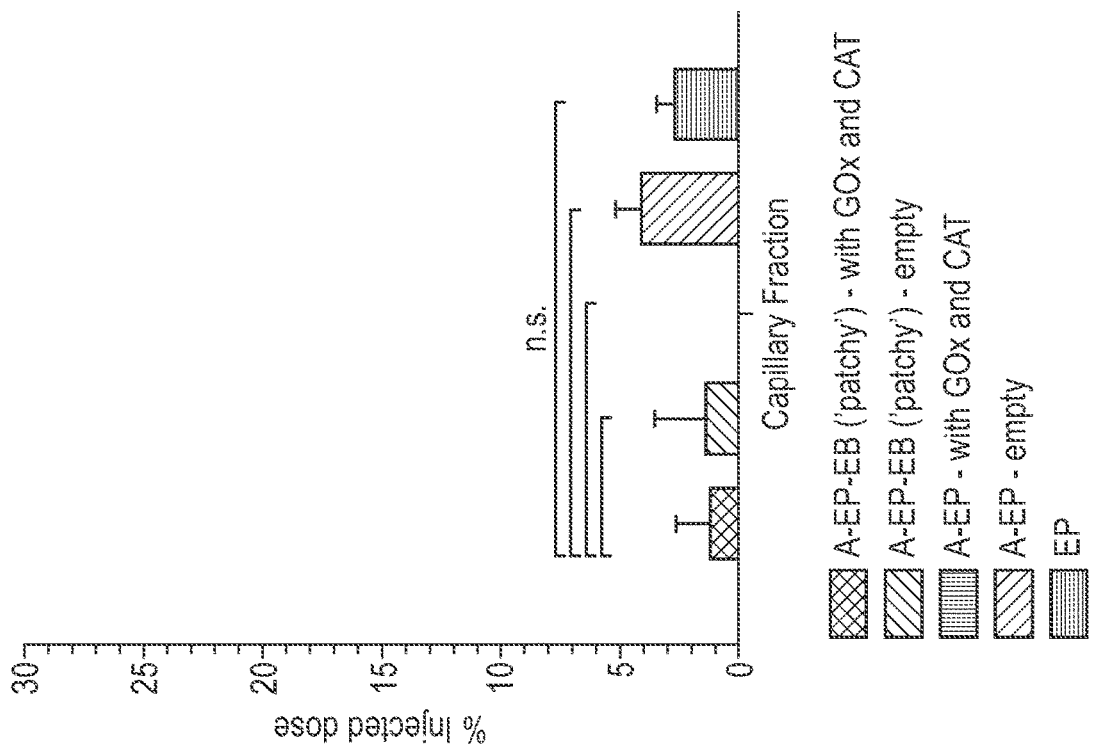
FIG. 5 shows uptake of fluorescently labelled polymersomes by mouse brain tissue as determined by fluorescence spectroscopy.
Figure 5B:
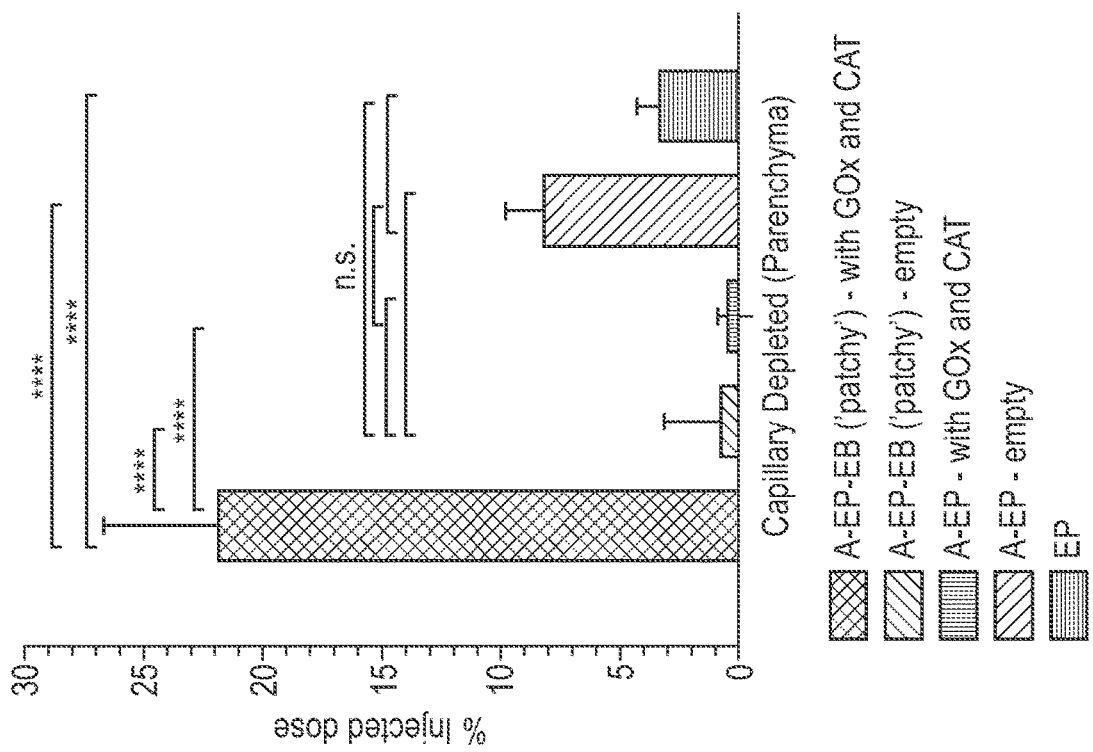

The improved uptake observed for the polymersomes according to the invention is shown in FIG. 5 (where GOx is glucose oxidase and CAT is catalase).

---

---

The invention claimed is:

1. A method comprising
administering a chemotactic, drug-containing polymersome to a subject; and
delivering said chemotactic, drug-containing polymersome to the brain tissue of said subject by transcytosis of said chemotactic, drug-containing polymersome across the blood-brain barrier of said subject; wherein said chemotactic, drug-containing polymersome comprises:
(a) a polymersome that comprises a targeting moiety on its external surface, wherein the targeting moiety is adapted to enable the polymersome to cross the blood-brain barrier;
(b) an enzyme encapsulated within the polymersome, wherein the enzyme comprises glucose oxidase; and
(c) a drug encapsulated within the polymersome;
wherein:
(i) the polymersome is permeable to a signalling molecule that is a substrate for the enzyme, wherein the signalling molecule is glucose;
(ii) the enzyme is capable of converting the signalling molecule into one or more product molecules;
(iii) the polymersome is permeable to the one or more product molecules;
(iv) the permeability to the one or more product molecules of a first region of the polymersome is greater than the permeability to the one or more product molecules of a second region of the polymersome, the second region being diametrically opposed to the first region; and
(v) the first region of the polymersome comprises a first polymer and the second region of the polymersome comprises a second polymer, the second polymer being different from the first polymer.

2. The method of claim 1, wherein the molar ratio of the first polymer to the second polymer is less than 1:1.

3. The method of claim 2, wherein the molar ratio of the first polymer to the second polymer is less than 1:4.

4. The method of claim 1, wherein the targeting moiety is an antibody or antibody fragment, a peptide, an aptamer, a small molecule, a vitamin or a carbohydrate that is attached to the external surface of the polymersome.

5. The method of claim 1, wherein the targeting moiety is a pendant group of a polymer comprised by the polymersome.

6. The method of claim 1, wherein the targeting moiety targets the LRP-1 receptor.

7. The method of claim 6, wherein the targeting moiety is a peptide comprising the sequence TFFYGGSRGKRNNFKTEEY (SEQ ID No. 1).

8. The method of claim 1, wherein the enzyme comprises glucose oxidase in combination with catalase.

9. The method of claim 1, wherein the drug is selected from a neuroprotectants, immunomodulatory drugs, NSAIDs, corticosteroids, DMARDs, immunosuppressants, TNF-alpha inhibitors and anti-cancer drugs.

* * * * *